US 9,895,142 B2

(12) United States Patent
Sato et al.

(10) Patent No.: US 9,895,142 B2
(45) Date of Patent: Feb. 20, 2018

(54) IMPLANT PLACEMENT DEVICE, COUPLING SUPPORT, AND ENDOSCOPIC TREATMENT TOOL

(75) Inventors: Masatoshi Sato, Tokyo (JP); Shinji Takahashi, Tokyo (JP); Tatsutoshi Hashimoto, Tokyo (JP); Kazushi Murakami, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 860 days.

(21) Appl. No.: 13/115,445

(22) Filed: May 25, 2011

(65) Prior Publication Data

US 2012/0029278 A1 Feb. 2, 2012

Related U.S. Application Data

(63) Continuation of application No. PCT/JP2010/069415, filed on Nov. 1, 2010.
(Continued)

(51) Int. Cl.
*A61F 2/00* (2006.01)
*A61B 17/00* (2006.01)
(Continued)

(52) U.S. Cl.
CPC .... *A61B 17/00234* (2013.01); *A61B 1/00133* (2013.01); *A61B 1/018* (2013.01);
(Continued)

(58) Field of Classification Search
CPC .. A61B 2017/00818; A61B 2017/0649; A61B 17/00234; A61B 17/0057;
(Continued)

(56) References Cited

U.S. PATENT DOCUMENTS

2004/0073237 A1* 4/2004 Leinsing ............. A61B 17/064
606/151
2005/0187613 A1* 8/2005 Bolduc et al. ............... 623/1.23
(Continued)

FOREIGN PATENT DOCUMENTS

CN 1742684 A 3/2006
EP 1 961 388 A2 8/2008
(Continued)

OTHER PUBLICATIONS

Notice of Allowance dated Jul. 12, 2011 from corresponding Japanese Patent Application Publication No. 2011-518969 together with English language translation.
(Continued)

*Primary Examiner* — Jonathan Miles
*Assistant Examiner* — Kendra Obu
(74) *Attorney, Agent, or Firm* — Scully, Scott, Murphy & Presser, P.C.

(57) ABSTRACT

An implant placement device includes a sheath; a long-axis member having an opening on a distal end side, movable along an axis, and a lumen communicating with the opening; a stylet movable in the axis and provided within the lumen to be turnable around the axis; an operating part on a proximal end side of the stylet to turn the stylet around the axis; a guide part on the proximal end side of the sheath to guide the operating part in a predetermined direction, thereby moving the sheath in the axis with respect to the stylet and turning a distal end portion of the stylet around the axis; and a coupling portion formed at the distal end of the stylet, detachably coupled with an implant, and moving in the axis and turning around the axis along with the stylet and the implant according to an operation of the operating part.

26 Claims, 28 Drawing Sheets

Related U.S. Application Data

(60) Provisional application No. 61/259,255, filed on Nov. 9, 2009.

(51) Int. Cl.
*A61B 17/064* (2006.01)
*A61B 17/068* (2006.01)
*A61B 1/00* (2006.01)
*A61B 1/018* (2006.01)
*A61B 17/06* (2006.01)

(52) U.S. Cl.
CPC .......... *A61B 17/064* (2013.01); *A61B 17/068* (2013.01); *A61B 17/0644* (2013.01); *A61B 2017/00477* (2013.01); *A61B 2017/00818* (2013.01); *A61B 2017/0645* (2013.01); *A61B 2017/0649* (2013.01); *A61B 2017/06052* (2013.01)

(58) Field of Classification Search
CPC . A61B 17/064; A61B 17/0644; A61B 17/068; A61B 17/08; A61B 2017/00238; A61B 2017/00584; A61B 2017/00477; A61B 2017/00668; A61B 2017/00646; A61B 2017/00823; A61B 2017/00827; A61B 2017/06052; A61B 2017/0645
See application file for complete search history.

(56) References Cited

U.S. PATENT DOCUMENTS

| | | | | |
|---|---|---|---|---|
| 2005/0267495 | A1* | 12/2005 | Ginn et al. | 606/151 |
| 2007/0123928 | A1* | 5/2007 | Farnan | 606/200 |
| 2008/0015633 | A1* | 1/2008 | Abbott et al. | 606/207 |
| 2008/0051626 | A1* | 2/2008 | Sato et al. | 600/101 |
| 2008/0208214 | A1* | 8/2008 | Sato et al. | 606/139 |
| 2009/0318956 | A1* | 12/2009 | Belef | A61B 17/0057 606/213 |

FOREIGN PATENT DOCUMENTS

| | | |
|---|---|---|
| EP | 1 992 295 A1 | 11/2008 |
| EP | 2 033 584 A1 | 3/2009 |
| JP | 63-34699 Y2 | 9/1988 |
| JP | H07-155331 A | 6/1995 |
| JP | 2000-166863 A | 6/2000 |
| JP | 2000-229084 A | 8/2000 |
| JP | 2004-357902 A | 12/2004 |
| JP | 2005-046488 A | 2/2005 |
| JP | 2005-193044 | 7/2005 |
| JP | 2006-187471 A | 7/2006 |
| JP | 2008-504943 | 2/2008 |
| JP | 2008-206983 A | 9/2008 |
| JP | 2009-066408 A | 4/2009 |
| WO | 97/32527 A1 | 9/1997 |
| WO | 2002/19923 A1 | 3/2002 |
| WO | 2005/081936 A2 | 9/2005 |
| WO | 2005/115256 A2 | 12/2005 |
| WO | 2006/115689 A1 | 11/2006 |

OTHER PUBLICATIONS

International Search Report PCT/JP2010/069415 dated Feb. 8, 2011.

Supplementary European Search Report dated Mar. 18, 2015 from related European Application No. 10 82 8260.9.

European Office Action dated Jan. 25, 2017 in corresponding European Application No. 10 828 260.9.

\* cited by examiner

IMPLANT PLACEMENT DEVICE, COUPLING SUPPORT, AND ENDOSCOPIC TREATMENT TOOL

This application is a Continuation of International Patent Application No. PCT/JP/2010/069415, claiming priority on the basis of U.S. Patent Application No. 61-259,255 provisionally applied for in the US on Nov. 9, 2009. The contents of both these U.S. Patent Application and International Patent Application are incorporated herein by reference.

BACKGROUND OF THE INVENTION

Field of the Invention

The invention relates to an implant placement device, a coupling support, and an endoscopic treatment tool. More specifically, the invention relates to an implant placement device that endoscopically places an implant in a tissue, a coupling support that couples the implant placement device and an endoscope together, and an endoscopic treatment tool that is used after being attached to the endoscope.

Background Art

Laparoscopic surgery in which treatment tools are inserted percutaneously is known as a technique for performing treatments on the internal organs or the like of a body. Since laparoscopic surgery is less invasive compared to incising the abdomen, early recovery can be expected.

A treatment tool used in laparoscopic surgery has a hard shaft percutaneously inserted into a body, and forceps or the like that perform treatment on a body tissue is provided at the distal end of the shaft. For example, a treatment tool used in applications such as connecting the lumen of organs disclosed in Japanese Patent Application Laid-Open No. 2005-193044. An intraluminal anastomosis device which is a treatment tool disclosed in Japanese Patent Application Laid-Open No. 2005-193044 has a gripper that is openably and closably attached to the distal end of the shaft, and a fastener inserted into the shaft. The fastener can be pushed out of the distal end of the shaft by an ejection mechanism on the proximal end side. The fastener is manufactured by heat-treating a shape memory alloy into a flat coiled form and inserting it into the shaft in an extended state. When the fastener is used, the fastener is pushed out by the ejection mechanism and inserted into the body. The fastener is heated at body temperature, restored to a coiled form, and placed in a body tissue. Anastomosis of hollow organs can be performed by the fastener restored to the coiled form.

As other examples of placing the fastener in a body tissue, a tissue fastening instrument for surgery is disclosed in the description of International Publication No. WO2002/019923. In this example, the fastener is pushed out of a needle and placed in the tissue. This tissue fastening instrument is provided with a stopper that controls the depth when a needle is inserted into a tissue and the amount of the fastener to be supplied to the tissue. When a treatment is performed using this tissue fastening instrument, the instrument accommodating the fastener and the needle butts against the tissue. If the needle is advanced and inserted into the tissue, the position of the fastener is fixed by the stopper. Thereafter, the needle is pulled out of the tissue. Since the fastener does not move due to the presence of the stopper, the distal end portion thereof is left behind inside the tissue. When the instrument is removed from the tissue, the rest of the fastener remains outside the tissue. When the fastener is restored to a coiled form, the tissue is fastened.

In the description of International Publication Number No. WO 2002/19923, a tissue fastener formed in a coiled form is arranged so as to extend to the inside of a needlelike tubular member, the tubular member is inserted into a body tissue, and the tubular member is pulled out straight after a portion of the tissue fastener is arranged on the face opposite to the face where the tubular member is inserted.

SUMMARY OF THE INVENTION

A first aspect of the present invention is an implant placement device including a sheath having a longitudinal axis; a long-axis member having an opening formed on a distal end side thereof, movable along the longitudinal axis, and provided with a lumen communicating with the opening; a stylet being movable in the longitudinal axis within the lumen, and provided within the lumen so as to be turnable around the longitudinal axis; an operating part provided on the proximal end side of the stylet in order to turn the stylet around the longitudinal axis; a guide part provided on the proximal end side of the sheath to guide a movement of the operating part in a predetermined direction, thereby moving the sheath in the longitudinal axis with respect to the stylet and turning a distal end portion of the stylet around the longitudinal axis; and a coupling part formed at the distal end of the stylet, detachably coupled with an implant to be placed within a body tissue, and moving in the longitudinal axis and turning around the longitudinal axis along with the stylet and the implant according to an operation of the operating part.

A second aspect of the present invention is the implant placement device used after being inserted to an insertion part of an endoscope. Here, the long-axis member is a tubular member having a coil-spring-shaped implant arranged in a stretched state therein, and capable of being pierced into a body tissue. The tubular member is inserted through an inside of the sheath. The implant placement device further includes a stylet arranged inside the tubular member closer to the proximal end side than the coil in an insertion direction of the tubular member, and a sheath operating part moving at least the sheath to the distal end side in the insertion direction into the insertion part in an axial direction of the tubular member with respect to the endoscope, and moving at least the sheath to the proximal end side in the insertion direction with respect to the endoscope after the movement. The operating part is capable of operating the tubular member, the stylet, and the sheath.

A third aspect of the present invention is an endoscopic treatment tool including the implant placement device of the present invention and used in combination with an endoscope. The long-axis member is a tubular member capable of being inserted into a body tissue. The tubular member is inserted through the inside of the sheath. The operating part has an operating body that is coupled to the tubular member and the sheath, respectively, and operates at least any of the tubular member and the sheath. The operating body is provided with a tubular member slider that advances and retreats the tubular member in an axial direction of the tubular member with respect to the operating body. A slide stopper is provided on the distal end side of the tubular member slider in an insertion direction of the tubular member. The slide stopper is capable of moving relative to the operating body in the axial direction of the tubular member and capable of being fixed to the operating body, and regulates an advance and retreat of the tubular member slider when fixed to the operating body. The endoscopic treatment tool further includes a coupling member that couples the tubular member slider and the slider stopper together when the tubular member slider has come into contact with the slider stopper, and suppresses a movement of the tubular member slider at least in an advance and retreat direction with respect to the slider stopper.

A fourth aspect of the present invention is a coupling support capable of being inserted to an operating part of an endoscope, and coupling a forceps channel of the endoscope with the implant placement device or endoscopic treatment tool of the present invention. The coupling support includes a first engaging portion that engages with the external surface of the operating part, a second engaging portion that engages with the external surface of the implant placement device, and a coupling portion that couples together the first engaging portion and the second engaging portion in a positional relationship in which the direction of the central axis of a port of the forceps channel on the side of the operating part of the endoscope coincides with a direction in which the sheath extends from the implant placement device.

PREFERRED EMBODIMENTS

One embodiment of the present invention will be described below.

Figure 1:
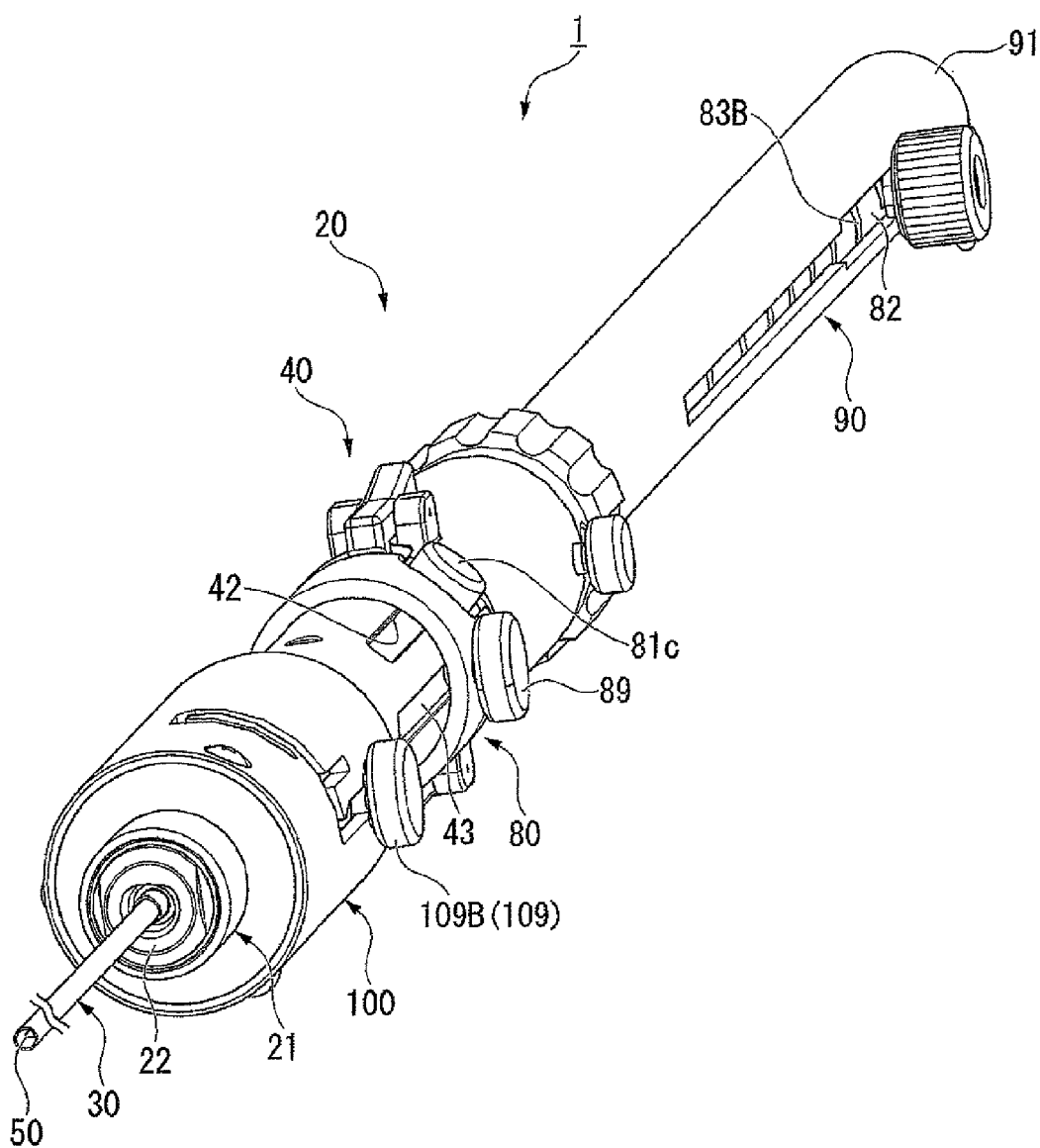
FIG. 1 is a perspective view showing an implant placement device of the present embodiment of one embodiment of the present invention.
Figure 2:
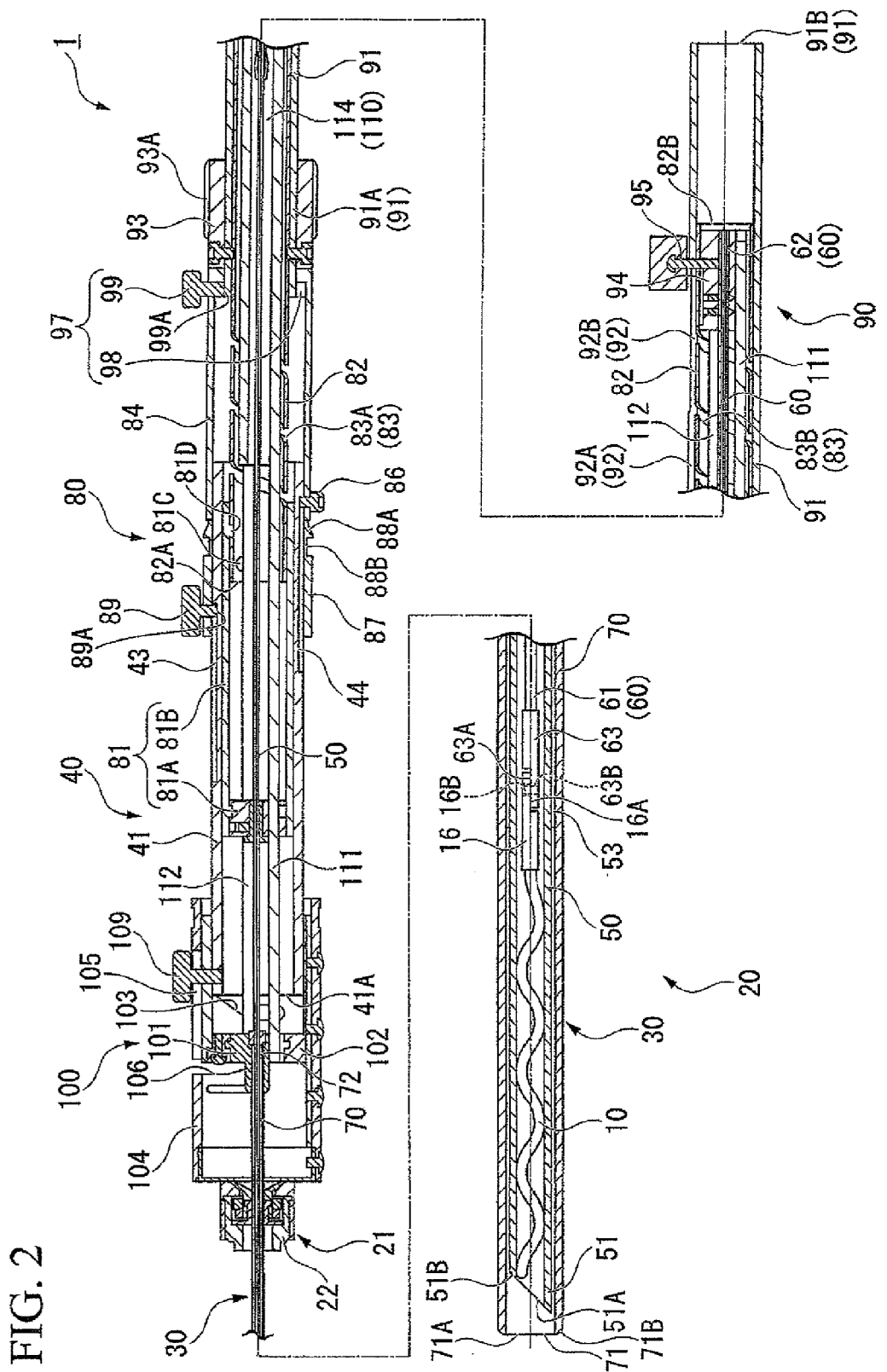
FIG. 2 is a sectional view showing the implant placement device.
Figure 3:
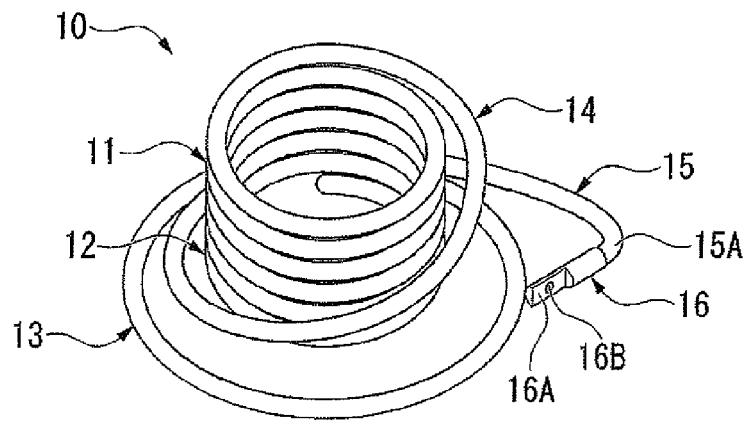
FIG. 3 is a perspective view showing a tissue fastener of the implant placement device.
Figure 4A:
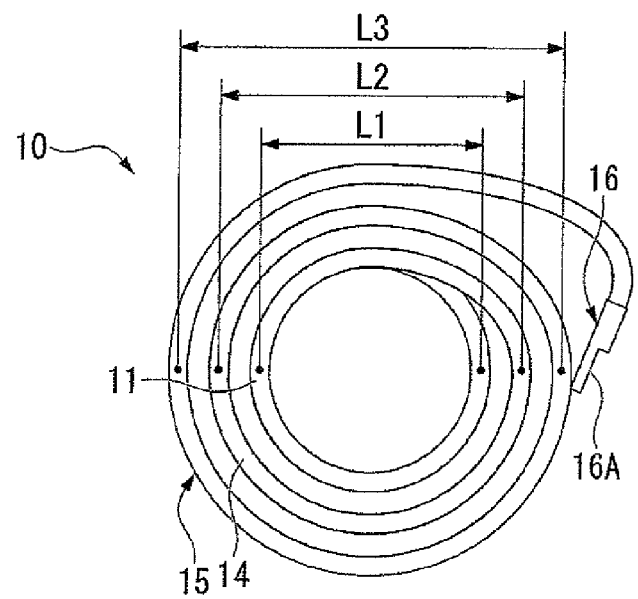
FIG. 4A is a plan view of the tissue fastener.
Figure 4B:
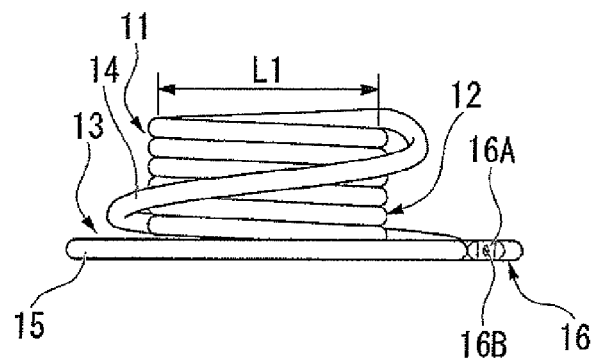
FIG. 4B is a side view of the tissue fastener.
Figure 5A:
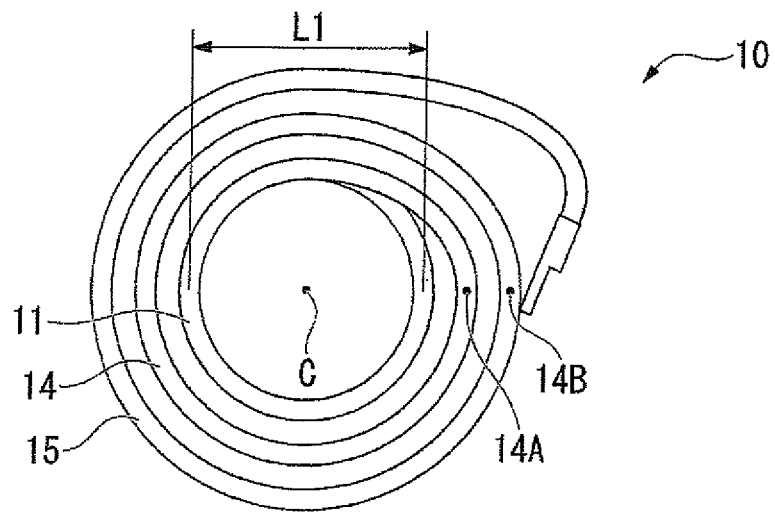
FIG. 5A is a plan view of the tissue fastener.
Figure 5B:
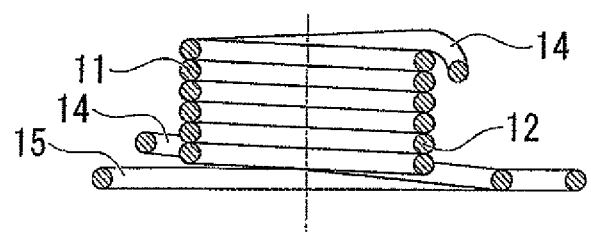
FIG. 5B is a lateral sectional view of the tissue fastener.
Figure 5C:
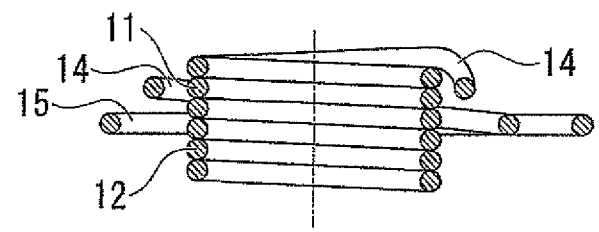
FIG. 5C is a sectional view showing the shape of the tissue fastener when the tissue fastener is placed in a body tissue.
Figure 5D:
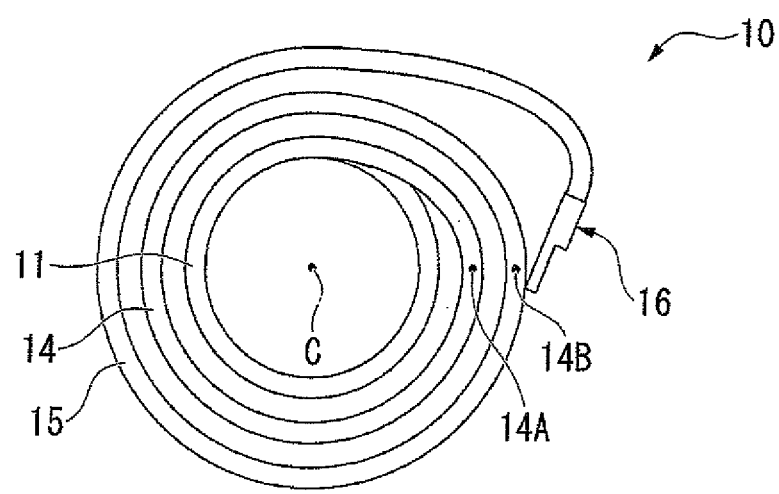
FIG. 5D is a plan view showing the tissue fastener with the shape shown in FIG. 5C.
Figure 6:
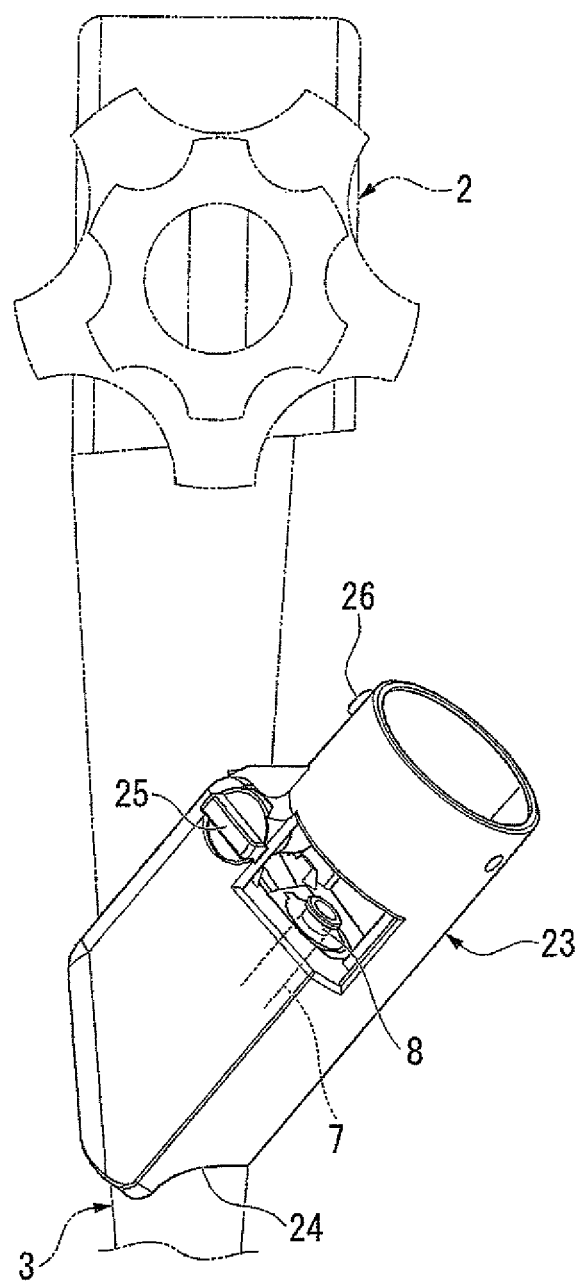
FIG. 6 is a perspective view showing a state where a coupling support of one embodiment of the present invention is attached to an endoscope.
Figure 7A:
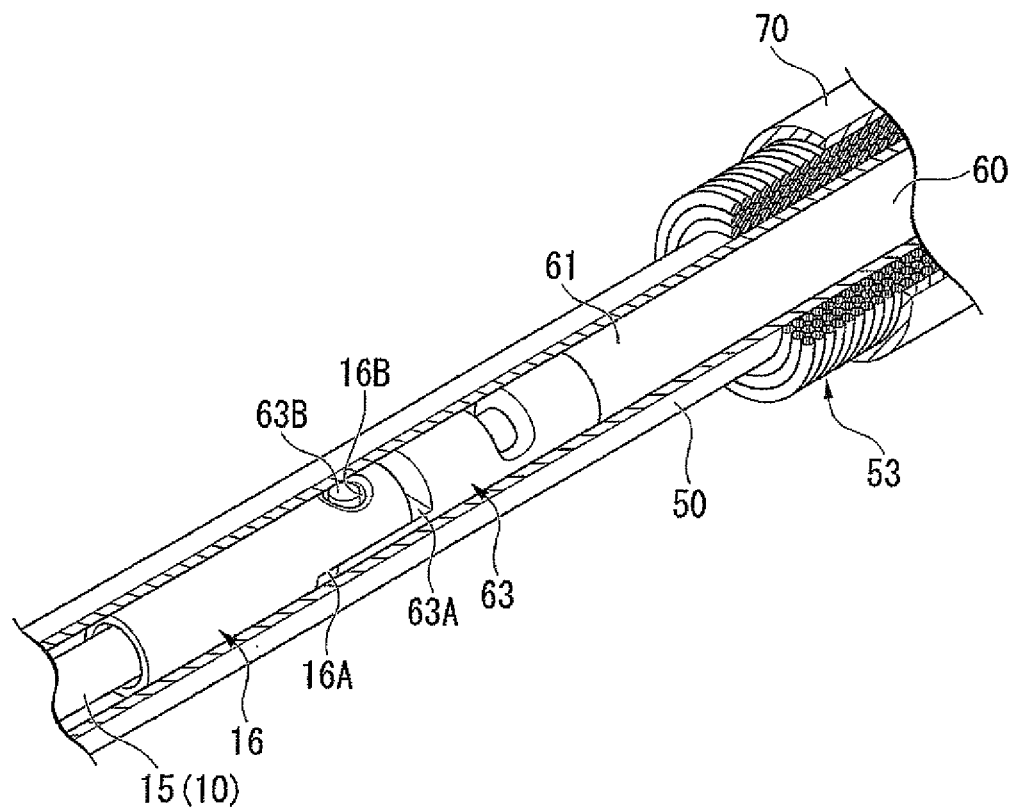
FIG. 7A is a fragmentary sectional view showing the configuration of a portion of an insertion part of the implant placement device.
Figure 7B:
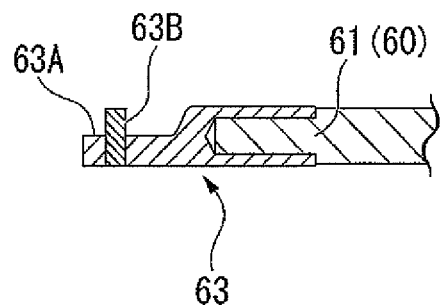
FIG. 7B is a sectional view showing the configuration of a portion of a stylet in an enlarged manner.
Figure 8:
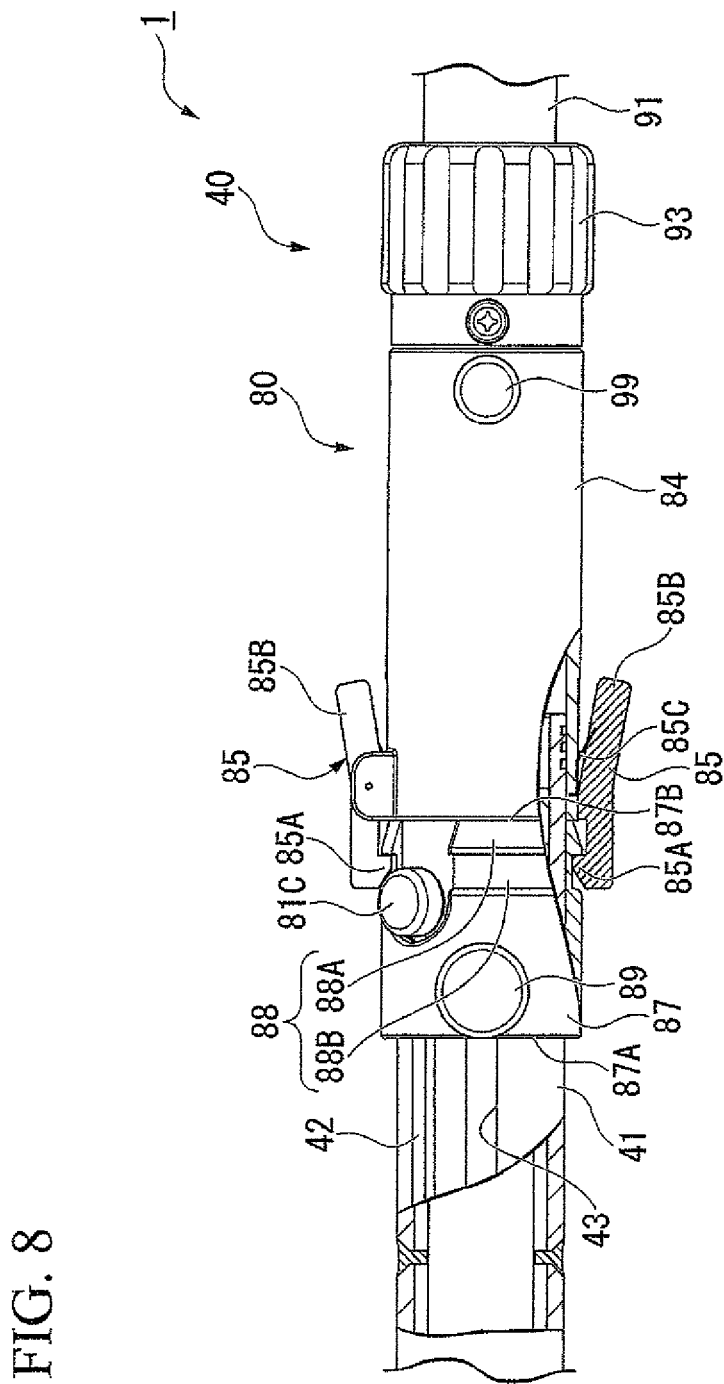
FIG. 8 is a fragmentary sectional view showing the portion of the tubular member operating part in the implant placement device in an enlarged manner.
Figure 9:
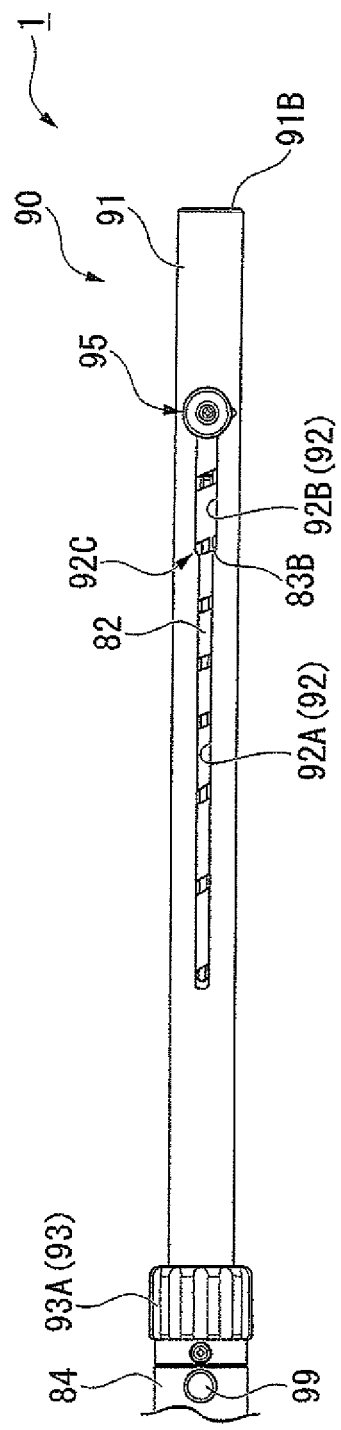
FIG. 9 is a side view showing the portion of a stylet operating part in the implant placement device in an enlarged manner.
Figure 10A:
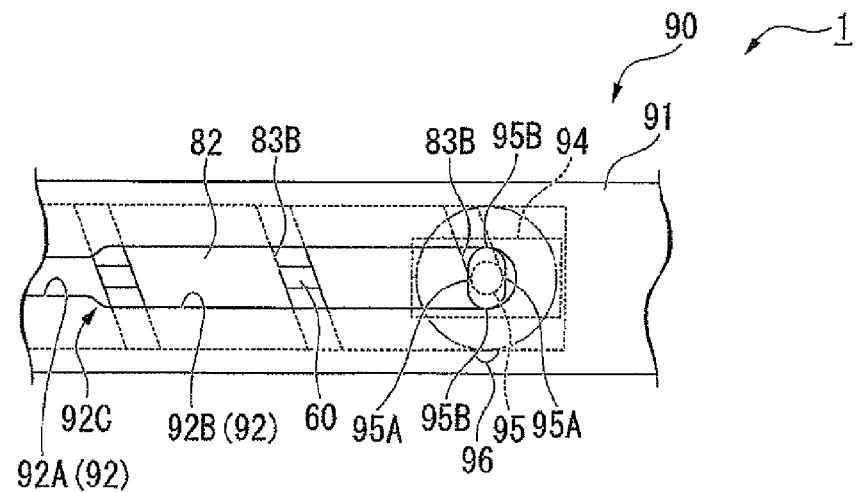
FIG. 10A is a side view showing the configuration of a portion of the stylet operating part in an enlarged manner.
Figure 10B:
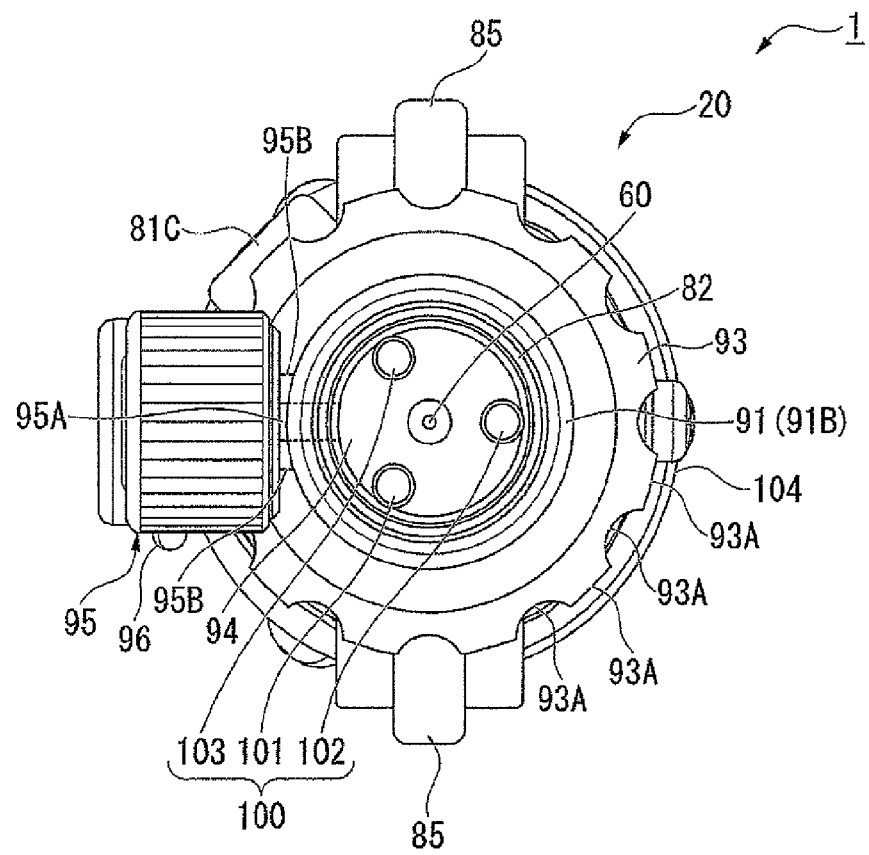
FIG. 10B is a back view when a portion of the stylet operating part is seen from the proximal end side of a sheath tube.
Figure 11:
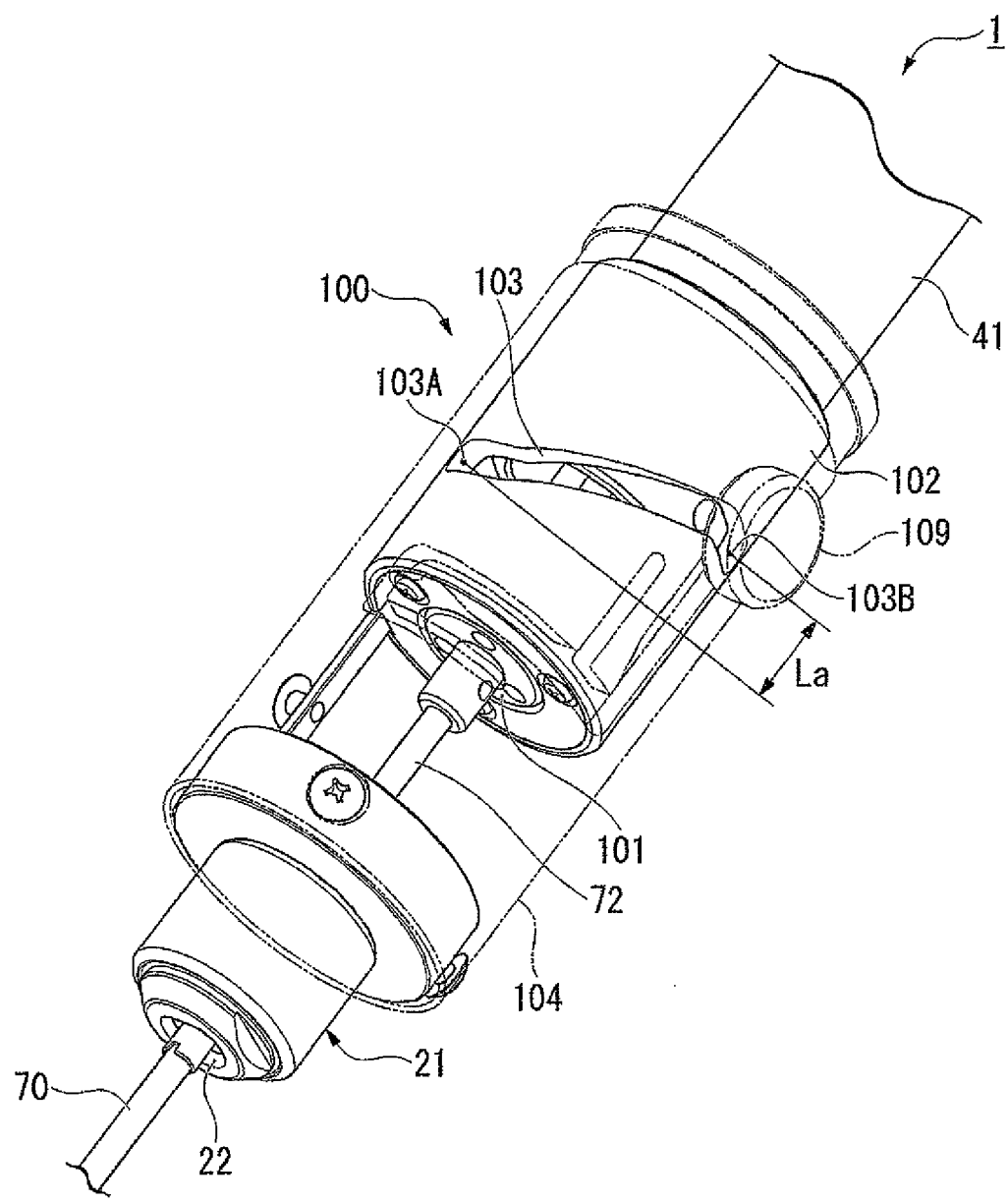
FIG. 11 is a perspective view showing the configuration of the portion of a sheath operating part in the implant placement device in an enlarged manner.
Figure 12:
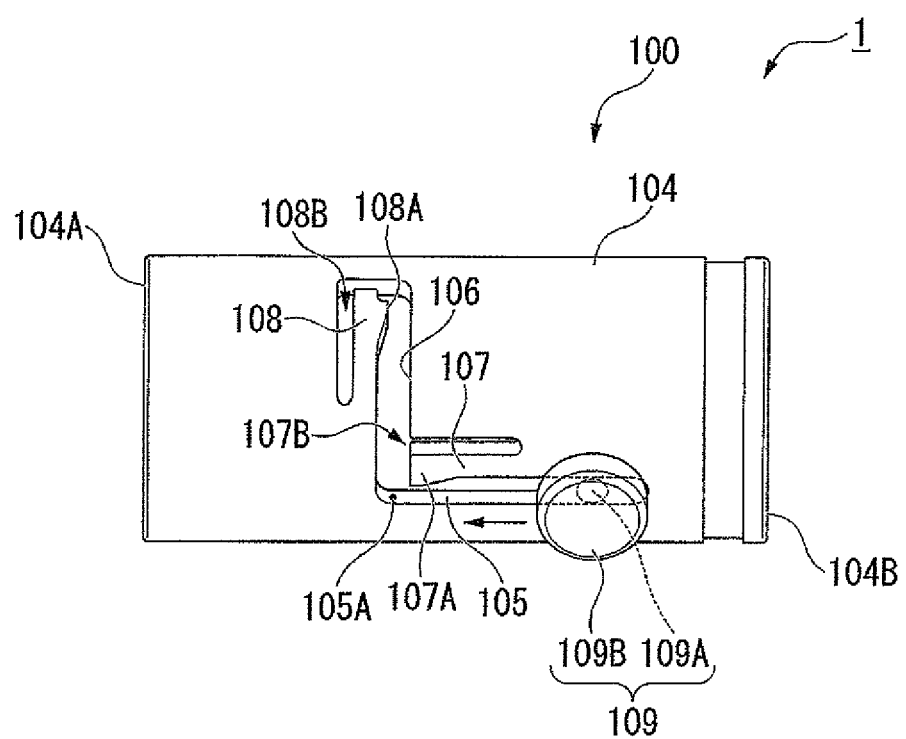
FIG. 12 is a side view showing the configuration of a portion of the sheath operating part.
Figure 13:
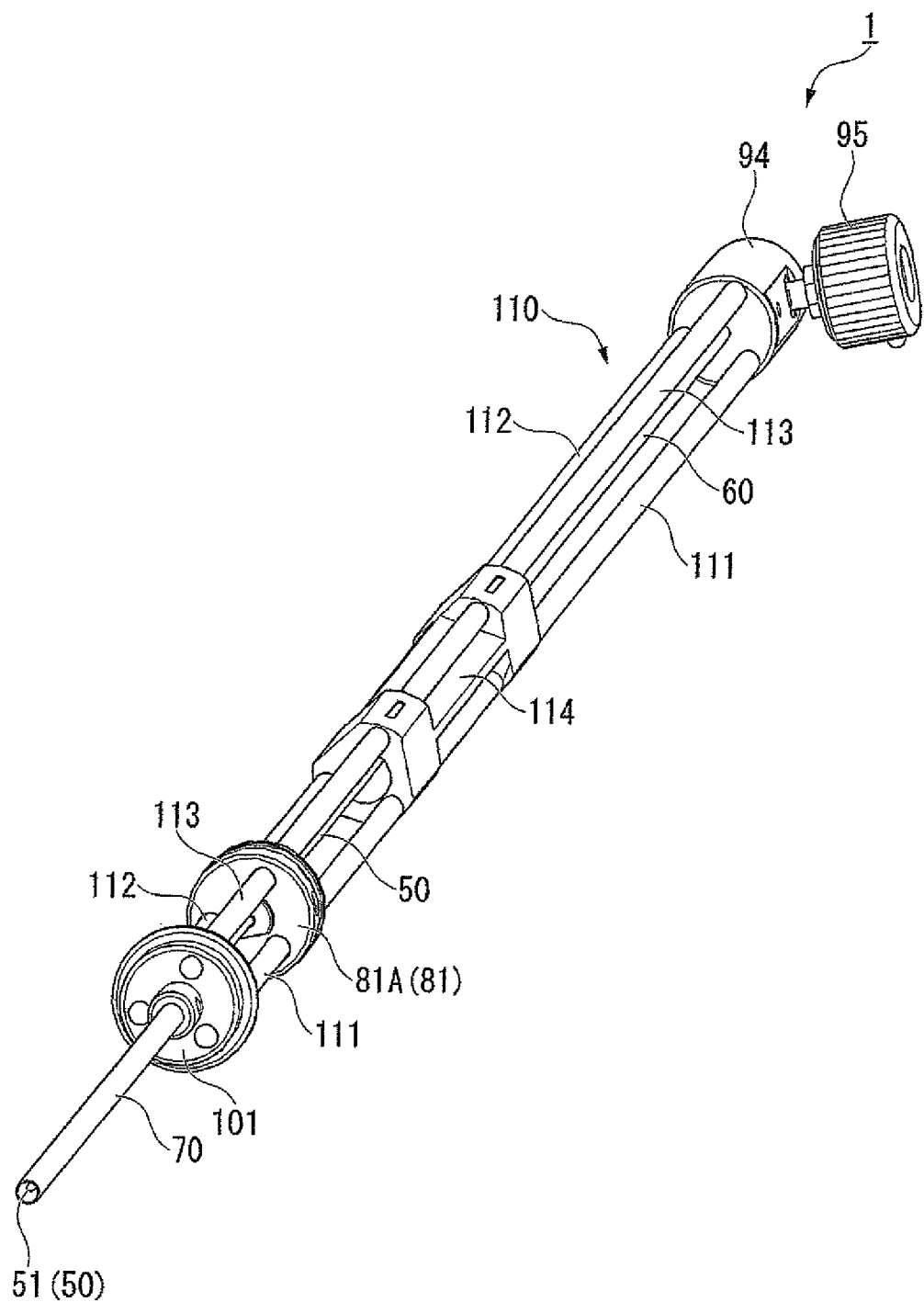
FIG. 13 is a perspective view showing the configuration of a rotation interlocking mechanism in the implant placement device.

First, the configuration of an implant placement device 1 of the present embodiment will be described with reference to FIGS. 1 to 13. FIG. 1 is a perspective view showing the implant placement device 1 of the present embodiment. FIG. 2 is a sectional view showing the implant placement device 1. FIG. 3 is a perspective view showing a tissue fastener 10 of the implant placement device 1. FIG. 4A is a plan view of the tissue fastener 10, and FIG. 4B is a side view of the tissue fastener 10. FIGS. 5A to 5D are views showing the tissue fastener 10, and FIG. 5A is a plan view of the tissue fastener 10, FIG. 5B is the lateral sectional view of the tissue fastener 10, FIG. 5C is a sectional view showing the shape of the tissue fastener 10 when the tissue fastener 10 is placed in a body tissue, and FIG. 5D is a plan view showing the tissue fastener 10 with the shape shown in FIG. 5C. FIG. 6 is a perspective view showing a state where a coupling support 23 of the present embodiment is attached to the endoscope 2. FIGS. 7A and 7B are views showing the configuration of a portion of an insertion part 30 of the implant placement device 1, and FIG. 7A is a fragmentary sectional view, and FIG. 7B is a sectional view showing the configuration of a portion of a stylet 60 in an enlarged manner. FIG. 8 is a fragmentary sectional view showing the portion of a tubular member operating part 80 in the implant placement device 1 in an enlarged manner. FIG. 9 is a side view showing the portion of a stylet operating part 90 in the implant placement device 1 in an enlarged manner. FIGS. 10A and 10B are views showing the configuration of a portion of the stylet operating part 90 in an enlarged manner, and FIG. 10A is a side view, and FIG. 10B is a back view as seen from proximal end 91B side of a sheath tube 91. FIG. 11 is a perspective view showing the configuration of the portion of a sheath operating part 100 in the implant placement device 1 in an enlarged manner. FIG. 12 is a side view showing the configuration of a portion of the sheath operating part 100. FIG. 13 is a perspective view showing the configuration of a rotation interlocking mechanism 110 in the implant placement device 1.

As shown in FIGS. 1 and 2, the implant placement device 1 includes a tissue fastener 10 that is an implant to be placed in a body, and an applicator 20 for placing the tissue fastener 10 in the body.

The implant placement device 1 of the present embodiment is a device that integrally fixes a first body tissue and a second body tissue, and performs the treatment that forms a fistula in the portions to which both the tissues are fixed. Here, the first body tissue and second body tissue are not limited to indicating separate organs. For example, a region of an organ may be taken as the first body tissue and a region other than this organ may be taken used as the second body tissue, so as to include fixing these two regions. In the present embodiment, the implant placement device of the present embodiment will be described taking as an example the treatment of fixing a common bile duct serving as the second body tissue to a duodenum serving as the first body tissue and causing both the organs to communicate with each other.

First, the tissue fastener 10 that is an implant in the implant placement device 1 of the present embodiment will be described.

FIGS. 3 to 5D are views showing the tissue fastener 10 of the present embodiment. As shown in FIG. 3, the tissue fastener 10 includes a first tissue fixing section 11 hooked to the duodenum, a second tissue fixing section 12 hooked to the common bile duct adjacent to the duodenum, and an outer peripheral spring section 13 that is connected to the first tissue fixing section 11.

The tissue fastener 10 is formed from one high elastic metal wire rod (hereinafter referred to as a "metal wire rod") in which all portions, i.e., the first tissue fixing section 11, the second tissue fixing section 12, and the outer peripheral spring section 13 are wound into a coiled form. In addition, it is preferable that this metal wire rod be formed from a superelastic alloy having superelasticity. The first tissue fixing section 11 and the second tissue fixing section 12 have the same loop diameter, and are formed such that their mutual loops are coaxial with each other. In the present embodiment, the portion of the metal wire rod of the tissue fastener 10, which hooks the duodenum and the common bile duct, is wound counterclockwise.

The outer peripheral spring section 13 includes a spring portion 14 that extends from an end of the first tissue fixing section 11, and an end coil portion 15 that extends from an end of the spring portion 14.

The spring portion 14 extends toward the second tissue fixing section 12 from the end of the first tissue fixing section 11 while forming a larger loop than the first tissue fixing section 11 and the second tissue fixing section 12. The loop that the spring portion 14 forms becomes gradually larger as it goes toward the second tissue fixing section 12. It is noted that this shape is not indispensable to the invention, for example, the spring portion 14 may extend toward the second tissue fixing section 12, while forming a loop of the same diameter.

Since the spring portion 14 extends toward the second tissue fixing section 12, as shown in FIGS. 4A and 4B, the metal wire rod that forms the spring portion 14 has an angle so as to incline with respect to the axis of a loop (hereafter referred to as a "basic loop L1") of the first tissue fixing section 11 and the second tissue fixing section 12.

It is preferable that the spring portion 14 be formed so as to have one or more integer turns.

The "one integer turn" means that an end 14A of the spring portion 14 on the side of the first tissue fixing section 11 and an end 14B of the spring portion on the side of the end coil portion 15 are aligned on the same straight line as the center C without pinching the center C of the basic loop L1 therebetween in plan view of the tissue fastener 10 as shown in FIG. 5A.

If the spring portion 14 has one or more integer turns, the spring portion 14 is uniformly distributed radially outside the basic loop L1 as in FIG. 5B in any kind of section when the tissue fastener 10 is seen in an axial cross-section that passes through the center C. Although the state where the spring portion 14 is set to have one turn is shown as an example in FIG. 5B, the same effects are exhibited even if the spring portion 14 is set to have two or more turns if the spring portion has integer turns. Accordingly, the force that the spring portion 14 exerts in the radial direction of the basic loop L1 with respect to the first tissue fixing section 11 and the second tissue fixing section 12 becomes uniform. For this reason, as shown in FIGS. 5C and 5D, even in a case where the tissue fastener 10 is placed in a tissue, the shape of the tissue fastener 10 can be stabilized without causing any axial deviation of the basic loop L1 of the first tissue fixing section 11 and the second tissue fixing section 12.

The angle at which the metal wire rod extends is changed at the end 14B at a connecting portion between the spring portion 14 and the end coil portion 15, and the end coil portion 15 is formed by bending so as to form a loop vertically to the central axis of the basic loop L1. Accordingly, the shape of the loop of the end coil portion 15 becomes parallel to the basic loop L1.

As shown in FIG. 3, the end 15A of the end coil portion 15 is provided with a coupling portion 16 for coupling to the stylet 60 that will be described below.

As shown in FIGS. 3 and 4A, the coupling portion 16 is formed substantially in a columnar shape that extends coaxially with the axis of the metal wire rod that constitutes the tissue fastener 10, and the edge of the coupling portion opposite to the edge where the metal wire rod is connected are formed in a half-split shape along the axial cross-section. More specifically, the coupling portion 16 has an end face 16A formed such that the central axis of this columnar shape is present and is turned to the radial outside of the basic loop L1, and a through hole 16B having one end that opens on the end face 16A, and formed so as to extend from the end face 16A in a direction orthogonal to the end face 16A.

The loop that the end coil portion 15 forms has a larger diameter than the loop that the spring portion 14 forms. Accordingly, as shown in a plan view of FIG. 4A, if the tissue fastener 10 is seen from the direction of the central axis of the basic loop L1, the basic loop L1 is present on the innermost side, the second loop L2 that the spring portion 14 forms is located outside the basic loop, and the third loop L3 that the end coil portion 15 forms is located outside the second loop L2. The basic loop L1, the second loop L2, and the third loop L3 do not overlap each other in the radial direction of the basic loop L1.

The applicator 20 of the implant placement device 1 will be described below.

As shown in FIG. 2, the applicator 20 is an instrument for placing the tissue fastener 10 in a body using an endoscope, and includes, for example, an attachment part 21 that fixes the applicator 20 to a forceps channel 7 (treatment tool channel) of the endoscope 2 shown in FIG. 6, an insertion part 30 that is inserted into the forceps channel 7 of the endoscope 2 to guide the tissue fastener 10 up to a target body tissue, and a main body 40 that is provided on the proximal end side in the insertion direction of the insertion part 30 to place the tissue fastener 10.

The attachment part 21, as shown in FIGS. 2 and 6, has a luer lock connector 22 screwed and fitted to a port 8 of the forceps channel 7, and a coupling support 23 (refer to FIG. 6) that couples the endoscope 2 and the applicator 20 together.

As shown in FIG. 6, the coupling support 23 has a frictional engaging portion 24 formed in a tubular shape such that the operating part 3 of the endoscope 2 is inserted thereinto and frictionally engages with the external surface of the operating part 3, a slip-out stopper pin 25 that pierces through the outer peripheral portion of the port 8 such that the frictional engaging portion 24 does not slip out of the operating part 3, and a stopper portion 26 that inserts and screw-stops the sheath slider 104 that will be described below. In this way, the applicator 20 and the endoscope 2 are fixed together via the coupling support 23 fixed to the applicator 20. Thereby, when the applicator 20 is attached to the endoscope 2, the applicator 20 can be supported by the coupling support 23 so as not to come off from the port 8 of the forceps channel 7 even if a user does not support the applicator 20.

As shown in FIG. 2, the insertion part 30 includes a tubular member 50, a stylet 60 that is arranged so as to be inserted through the tubular member 50, and a sheath 70 that receives the tubular member 50 and the stylet 60. All the tubular member 50, the stylet 60, and the sheath 70 have flexibility, and are arranged coaxially with each other. The insertion part 30 is formed such that the axial length thereof is greater than that of the above-described forceps channel 7.

The tubular member 50 is received and used in a state where the tissue fastener 10 is stretched. Preferably, the material of the tubular member 50 has a hardness to such a degree that the tubular member 50 is not bent when the tubular member 50 is inserted into a body tissue, and has flexibility to such a degree that the tubular member can be curved along the travel of the forceps channel 7 when being inserted through the forceps channel 7 of the endoscope 2. As the material of the tubular member 50, for example, stainless steel or superelastic alloys represented by nickel titanium alloy (NiTi) can be employed.

The tubular member 50 is adapted to be inserted into a body tissue from the distal end 51 side, and the distal end 51 of the tubular member 50 has an inclined end face 51A that is formed obliquely with respect to the longitudinal direction of the tubular member 50. Thereby, the distal end of the tubular member 50 is sharply finished.

In addition, an electrode may be provided at the distal end 51 of the tubular member 50, and an electric current may be applied to the distal end 51, thereby performing the cauterant incision of the body tissue, so that the tubular member 50 is inserted into a body tissue. In this case, the distal end 51 of the tubular member 50 does not need to be sharply formed.

The stylet 60 is arranged closer to the proximal end side than the tissue fastener 10 inside the tubular member 50, and is formed in the shape of a rod capable of advancing and retreating inside the tubular member 50. A coupling portion 63 coupled to the above-described coupling portion 16 provided at the tissue fastener 10 is fixed to a distal end 61 of the stylet 60.

As shown in FIGS. 7A and 7B, the coupling portion 63 has an end face 63A formed so as to abut on the end face 16A of the coupling portion 16, and a projection 63B inserted into the through hole 16B of the coupling portion 16.

The end face 63A is positioned such that the circumferential relative position thereof with respect to the tubular member 50 is directed to proximal end 51B (refer to FIG. 2) side of the inclined end face 51A formed at the distal end 51 of the tubular member 50.

When the tissue fastener 10 is received inside the tubular member 50, the projection 63B is inserted into the through hole 16B. Additionally, the end face 16A and the end face 63A come into contact with each other. For this reason, the tissue fastener 10 is integrated with the stylet 60, and is capable of advancing and retreating within the tubular member 50, and when the stylet 60 rotates around an axis, the tissue stylet 60 and the tissue fastener 10 rotate integrally. Inside the tubular member 50, the projection 63B is stopped from slipping out of the through hole 16B in a state where the coupling portion 16 and the coupling portion 63 are combined together, even if the end face 16A and the end face 62B move relatively in separating directions. For this reason, the engagement between the tissue fastener 10 and the stylet 60 is not released inside the tubular member 50.

A three-layer coil sheath 53 wound around the external surface of the tubular member 50 in three layers is provided between the tubular member 50 and the sheath 70. As the material of the three-layer coil sheath 53, for example, a metal wire rod can be adopted, and a coil sheath with three-layer structure can be formed by winding this wire rod. Additionally, although the three-layer coil sheath 53 is fixed to the tubular member 50, this coil sheath is not fixed to the sheath 70.

The sheath 70 is a tubular member having flexibility, and the tubular member 50 is inserted through the sheath. The distal end 71 of the sheath 70 has a flat face 71A that is formed flatly so as to be orthogonal to the longitudinal direction of the sheath 70, and a chamfer 71B formed in such a shape that the angles of the outer peripheral portion of the flat face 71A are removed in order to facilitate insertion of the sheath 70 through the forceps channel 7 of the endoscope 2.

As shown in FIG. 2, the main body 40 has the operating body 41 that is formed substantially in a tubular shape. The operating body 41 is provided with a tubular member operating part 80 for operating the tubular member 50, a stylet operating part 90 for operating the stylet 60, a sheath operating part 100 for operating the sheath 70, and a rotation interlocking mechanism 110 that couples the tubular member operating part 80, the stylet operating part 90 and the sheath operating part 100 together, and interlocks the respective rotational operations thereof.

Additionally, a long hole 42 (refer to FIG. 1) through which a coupling screw 81C (that will be described below) of the tubular member operating part 80 passes, a guide groove 43 (refer to FIG. 1) into which a positioning screw 89 (that will be described below) is fitted, and a regulating groove 44 (refer to FIG. 2) into which a regulating member 86 (that will be described below) is fitted are formed in the operating body 41 so as to extend in the longitudinal direction of the operating body 41.

As shown in FIGS. 2 and 8, the tubular member operating part 80 includes a fixing portion 81 fixed to a proximal end 52 of the tubular member 50, a tubular cam tube 82 coupled to the fixing portion 81, a tubular member slider 84 coupled to the fixing portion 81, and a substantially tubular slide stopper 87 that is fitted to the outer peripheral surface of the operating body 41 on the distal end 41A side of the operating body 41 rather than the tubular member slider 84.

The fixing portion 81 has a substantially disk-shaped fixing member 81A to which the tubular member 50 is fixed, and a tubular supporting member 81B coupled to the fixing member 81A so as to be relatively turnable around the central axis of the fixing member 81A. The supporting member 81B has a shape along the inner wall of the operating body 41 inside the operating body 41, the supporting member 81B is relatively movable in the longitudinal direction of the operating body 41 inside the operating body 41, and the circumferential relative position of the supporting member 81B with respect to the operating body 41 is positioned.

A fixing screw 81C, which is screwed radially inward via the long hole 42 from the outside of the operating body 41 as shown in FIG. 8 and passes through the supporting member 81B and the cam tube 82 as shown in FIG. 2, is detachably provided on the proximal end side of the fixing portion 81. In a state where the fixing screw 81C is attached, the fixing portion 81 and the cam tube 82 are fixed so that the fixing portion 81 and the cam tube 82 can integrally move relative to the operating body 41 within a range of the longitudinal length of the long hole 42.

As shown in FIG. 2, the cam tube 82 is a member that rotates the stylet 60 around the axis of the stylet 60, and relatively moves the stylet 60 in the axial direction of the tubular member 50. The outer wall portion of the cam tube 82 is formed with a spiral cam 83 formed such that a portion of the outer wall thereof is cut off.

The spiral cam 83 has a first spiral cam 83A located on the distal end 82A side of the cam tube 82, and a second spiral cam 83B located closer to the proximal end 82B than the first spiral cam 83A.

The first spiral cam 83A engages with the supporting member 81B. More specifically, a pin 81D that is provided so as to protrude radially inward in the supporting member 81B is fitted into the first spiral cam 83A. As seen from the distal end 82A side of the cam tube 82 to the proximal end 82B side, the shape of the first spiral cam 83A is a spiral shape that proceeds in the clockwise direction around the axis of the cam tube 82 as it goes from the proximal end 82B side of the cam tube 82 to the distal end 82A side thereof.

As shown in FIGS. 2 and 9, the second spiral cam 83B has a spiral shape of the same direction as the first spiral cam 83A. Moreover, the shape of the second spiral cam 83B is determined on the basis of the shape of the tissue fastener 10. That is, the second spiral cam 83B has the number of turns equal to or more than the number of turns of the metal wire rod in the tissue fastener 10. Moreover, the length of the lead of the second spiral cam 83B is set to be equal to the length of the metal wire rod equivalent to one round of the tissue fastener 10 in the circumferential direction. In the present embodiment, the loop of the tissue fastener 10 has different loop diameters in the basic loop (first loop) L1, the second loop L2, and the third loop L3 as described above, and has different lengths of the metal wire rod in the respective loops. For this reason, the second spiral cam 83B of the present embodiment is formed by changing the length of the lead there such that the third loop, the second loop, and the first loop are arranged in order from the distal end 82A side of the cam tube 82.

As shown in FIGS. 2 and 8, the tubular member slider 84 has a pair of hooks 85 that couples the tubular member slider 84 together to the slide stopper 87, and the regulating member 86 that is fitted into the regulating groove 44 of the operating body 41.

A pair of hooks 85 is provided at the positions where the hooks face each other in the radial direction on the external surface of the tubular member slider 84. Additionally, each of the pair of hooks 85 is biased by, for example, a flat spring 85C such that a distal end 85A of the hook 85 is directed to the radial inside of the tubular member slider 84. A proximal end 85B of the hook 85 is a portion operated by a user, and the distal ends 85A of the pair of hooks 85 can be simultaneously moved to the radial outside of the tubular member slider 84 by pinching the proximal ends 85B, respectively, with user's thumb and index finger.

As shown in FIG. 8, the slide stopper 87 has an engaging portion 88 for engaging the distal end 85A of the hook 85. The engaging portion 88 has a taper portion 88A that inclines so as to be directed to the radial outside as it goes from the proximal end 87B of the slide stopper 87 toward the distal end 87A, and an engaging groove 88B formed so as to be recessed radially inward on the distal end 87A side rather than the taper portion 88A.

While the hook 85 of the tubular member slider 84 engages with the engaging groove 88B of the slide stopper 87, the slide stopper 87 and the tubular member slider 84 are stopped from relatively moving in the axial direction.

Moreover, the positioning screw 89 having a distal end 89A capable of abutting on the external surface of the operating body 41 is attached to the slide stopper 87. By screwing in the positioning screw 89 in the inward direction of the slide stopper 87, the positioning screw 89 abuts on the bottom of the guide groove 43 and pressed against the bottom radially inward, so that the relative position between the slide stopper 87 and the operating body 41 can be fixed.

As shown in FIGS. 2 and 9, the stylet operating part 90 has the sheath tube 91 that covers the outer periphery of the cam tube 82, a rotation input portion 93 fixed to the distal end of the sheath tube 91, and a fixing portion 94 arranged inside the cam tube 82 and having the proximal end 62 of the stylet 60 fixed thereto. Additionally, a rotation regulating portion 97 that regulates the circumferential relative rotational operation between the sheath tube 91 and the tubular member slider 84 is provided between the distal end of the sheath tube 91 and the tubular member slider 84.

As shown in FIG. 9, the sheath tube 91 has a long hole 92 formed so as to extend in the longitudinal direction of the sheath tube 91, in the outer wall thereof. The long hole 92, as shown in FIGS. 2 and 9, is composed of a long hole 92A located on the distal end 91A side of the sheath tube 91, and a long hole 92B located on the proximal end 91B side of the sheath tube 91. The respective widths of the long hole 92A and the long hole 92B when the longitudinal direction of the long hole 92 is defined as the longitudinal direction of the sheath tube 91 are different from each other at the long hole 92A and the long hole 92B. The width of the long hole 92A is formed so as to be smaller than the width of the long hole 92B.

The rotation input portion 93 is a portion that is gripped in order for a user to rotate the sheath tube 91. The external surface of the rotation input portion 93 is formed with a concavo-convex portion 93A (refer to FIG. 2) that serves as a circumferential slip stopper when the rotation input portion 93 is gripped by a user's hand.

As shown in FIGS. 2, 10A, and 10B, the fixing portion 94 has a guide pin 95 that protrudes toward the radial outside of the cam tube 82. The guide pin 95 passes through the spiral cam 83 of the cam tube 82, and passes through the long hole 92B of the sheath tube 91. Additionally, the guide pin 95 has a first wall portion 95A narrower than the width of the long hole 92A, and a second wall portion 95B wider than the width of the long hole 92A and narrower than the width of the long hole 92B.

The first wall portion 95A and the second wall portion 95B are arranged at positions shifted from each other by 90 degrees around the axis of the guide pin 95. For this reason, the guide pin 95 is caught between the long hole 92A and the long hole 92B in a state where the second wall portion 95B is directed to the width direction of the long hole 92B. Additionally, the guide pin 95 is turned by 90 degrees around an axis, and the first wall portion 95A is directed to the width direction of the long hole 92B, so that the guide pin 95 can enter the long hole 92A.

Additionally, the protruding end of the guide pin 95 is provided with a convex portion 96 that protrudes toward the radial outside of the guide pin 95. The convex portion 96 can be used as an index for allowing a user to grasp the positions of the first wall portion 95A and the second wall portion 95B when the guide pin 95 turns around an axis.

As shown in FIG. 2, the rotation regulating portion 97 has an abutting portion 98 that is provided at the distal end of the sheath tube 91 and of which a portion of the external surface is formed flatly, and a rotation regulating screw 99 that is screwed into the tubular member slider 84 such that the distal end 99A abuts on the abutting portion 98. The rotation regulating screw 99 can be attached and detached to the tubular member slider 84. For this reason, the tubular member slider 84 and the sheath tube 91 do not relatively rotate in a state where the rotation regulating screw 99 is attached, and the tubular member slider 84 and the sheath tube 91 are relatively rotatable in a state where the rotation regulating screw 99 is removed.

As shown in FIGS. 2 and 11, the sheath operating part 100 is provided on the distal end 41A side of the operating body 41 of the main body 40. The sheath operating part 100 has a substantially disk-shaped fixing portion 101 that has the proximal end 72 of the sheath 70 fixed at the center thereof, a substantially tubular cam tube 102 fixed to the fixing portion 101 so as to be relatively rotatable around the axis of the sheath 70, and a tubular sheath slider 104 provided coaxially with the cam tube 102 at the outer periphery and the cam tube 102.

As shown in FIG. 11, the cam tube 102 has a tilt cam groove 103 of a shape in which a portion of a wall portion is cut off so as to form a portion of a spiral that proceeds in the clockwise direction as it goes from the proximal end 102B to the distal end 102A as seen from the proximal end 102B toward the distal end 102A. In the present embodiment, it is preferable that the length La measured in the axial direction of the cam tube 102 between both circumferential ends 103A and 103B of the tilt cam groove 103 be set to be shorter than the length of the metal wire rod equivalent of one turn of the basic loop L1 of the tissue fastener 10.

As shown in FIG. 12, the sheath slider 104 has a first cam groove 105 that extends in the longitudinal direction of the main body 40, and a second cam groove 106 that extends in the circumferential direction of the sheath slider 104. The cam groove 105 and the cam groove 106 are formed so as to be connected together.

In the end 105A of the cam groove 105 located on the distal end 104A side of the sheath slider 104, an elastic stopper 107 that has a projection 107A that protrudes inward in the width direction of the cam groove 105 is provided, and in the end of the cam groove 106 far from the cam groove 105 in the circumferential direction of the sheath slider 104, an elastic stopper 108 that has a projection 108A that protrudes inward in the width direction of the cam groove 106 is provided. The elastic stoppers 107 and 108 are respectively formed with relief portions 107B and 108B serving as relief when the projections 107A and 108A move outward in the width direction of the cam grooves 105 and 106.

Additionally, as shown in FIGS. 11 and 12, in the sheath operating part 100, a sheath stopper 109 that is screwed into the operating body 41 so as to pass through such that the cam grooves 105 and 106 of the sheath slider 104 and the tilt cam groove 103 of the cam tube 102 is provided. The sheath stopper 109 has a threaded portion 109A, and a larger-diameter portion 109B that is formed with a larger diameter than the threaded portion 109A, and the cam tube 102 and the sheath slider 104 are pressed against and fixed to the operating body 41 by the larger-diameter portion 109B as the sheath stopper 109 is screwed into the operating body 41.

As shown in FIGS. 2 and 13, the rotation interlocking mechanism 110 has shaft members 111, 112, and 113 that are provided so as to extend in the longitudinal direction of the main body 40. The shaft members 111, 112, and 113 are respectively inserted through the fixing portion 81 of the tubular member operating part 80 and the fixing portion 94 of the stylet operating part 90, and are fixed to the fixing portion 101 of the sheath operating part 100. Additionally, a holding portion 114 that holds the shaft members 111, 112, and 113 in a predetermined positional relationship is fixed to the shaft members 111, 112, and 113. In the present embodiment, the shaft members 111, 112, and 113 are arranged at equidistant positions in the radial direction from the longitudinal axis of the main body 40, in other words, from the central axis of the tubular member 50 and the stylet 60 inside the main body 40 (refer to FIG. 10B). The fixing portion 81, the fixing portion 94, and the fixing portion 101 are adapted to rotate integrally by the rotation interlocking mechanism 110. That is, in the present embodiment, the tubular member 50 fixed to the fixing portion 81, the stylet 60 fixed to the fixing portion 94, and the sheath 70 fixed to the fixing portion 101 rotate integrally.

The operation when the implant placement device 1 of the present embodiment of the configuration described above is used will be described with reference to FIGS. 14 to 34.

Figure 14:
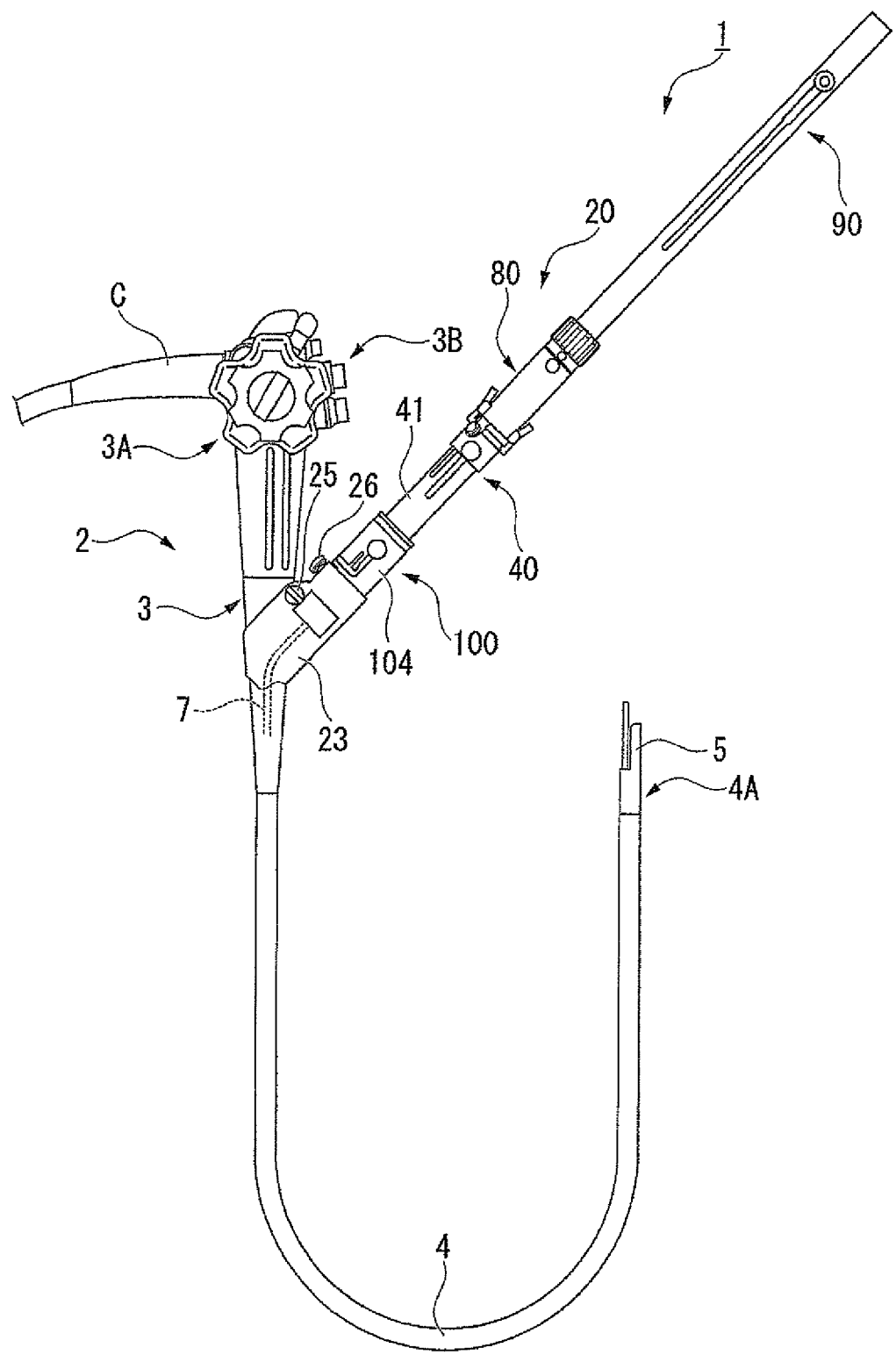
FIG. 14 is a side view showing a state where the implant placement device and the endoscope are combined together.

FIG. 14 is a side view showing a state where the implant placement device 1 and the endoscope are combined together.

In the present embodiment, as shows in FIG. 14, the implant placement device 1 is used with, for example, a linear scan type ultrasonic endoscope 2 (hereinafter referred to as an "endoscope 2") that has the forceps channel 7.

The endoscope 2 includes the operating part 3 that is used outside a body, a flexible insertion part 4 that extends from the operating part 3, a knob 3A that is provided at the operating part 3 to curve the distal end portion of the insertion part 4, a button 3B that performs air and water supply and air and water suction, and an ultrasonic observation part 5 that is provided so as to swell to the distal end side further from the distal end 4A of the insertion part 4. The ultrasonic observation part 5 radiates ultrasonic waves to the distal end side from the distal end 4A of the insertion part 4 by using an ultrasonic transducer attached to the distal end 4A of the insertion part 4, receives a reflected wave reflected from, for example, a body tissue or the like, and displays image information on an external monitor through the inside of the insertion part 4 and a universal cord C of the operating part 3. In this way, the shape, composition, or the like of the body tissue within a range where the ultrasnoic wave has been irradiated can be observed by the ultrasonic observation part 5.

Additionally, the endoscope 2 of the present embodiment is a forward viewing type endoscope, and the distal end 4A of the insertion part 4 is provided with an optical observation mechanism (not shown) that has a visual field on the distal end side further apart from the distal end 4A of the insertion part 4. The optical observation mechanism has an imaging lens group and a solid state imaging device built, for example, in the distal end 4A of the insertion part 4, and can be configured so as to project an optical image onto the external monitor through the inside of the universal cord C that extends from the inside of the insertion part 4 and the operating part 3.

In addition, the configuration of the endoscope 2 is not limited to that including the ultrasonic observation part 5, and may include other probe type ultrasonic devices, and observation may be performed using means other than the ultrasnoic wave. Additionally, endoscopes that do not include the ultrasonic observation part 5 can be used. In this case, it is preferable to observe the inside of a body by using together apparatuses, such as an ultrasonic device, an X-ray apparatus, a magnetic resonance imaging apparatus (MRI apparatus), and computerized tomography apparatus (CT apparatus), which are used outside a body.

Figure 15:
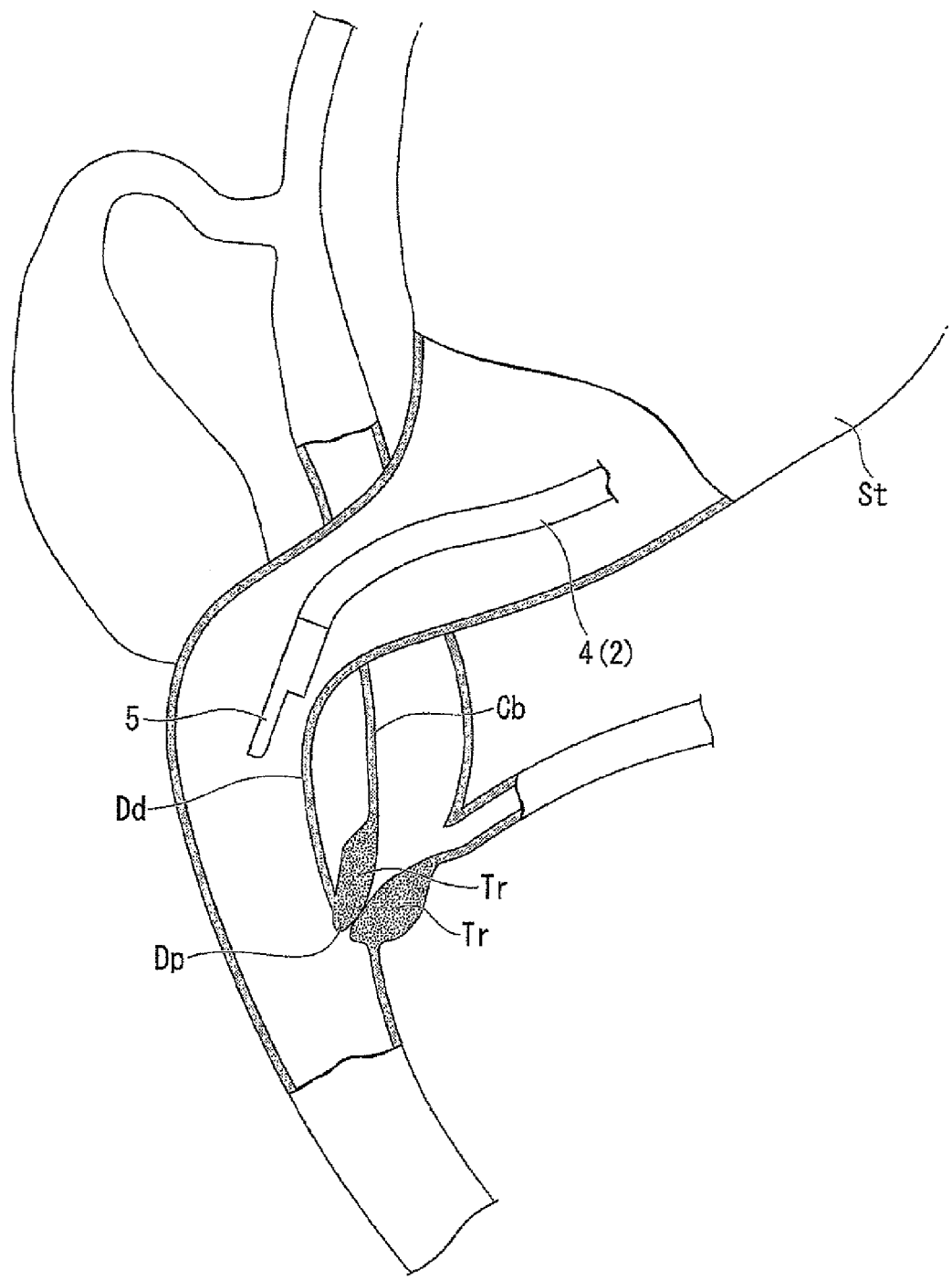
FIG. 15 is a view showing one process of a procedure before the implant placement device is used.

In the following, as for the procedure of performing a treatment by combining the implant placement device 1 of the present embodiment with the above-described endoscope 2, in an example of drainage of a transduodenal bile duct, the procedure of integrally fixing the duodenum and the common bile duct to form a through hole allowing both to communicate with each other will be described as an example. For example, as shown in FIG. 15, such a procedure is a jaundice relieve treatment that is carried out in a case where a duodenal papilla Dp is obstructed by a tumor Tr so that bile cannot be drained, and consequently the bile assimilates in the blood causing jaundice. This procedure enables bile to be directly drained from the common bile duct Cb to the duodenum Dd.

When the implant placement device 1 of the present embodiment is used, first, the tissue fastener 10 is arranged in a stretched state inside the tubular member 50, and the tubular member 50 is prepared in the positional relationship stored inside the sheath 70 (refer to FIG. 2). At this time, as the positional relationship of the respective parts in the implant placement device 1, the tubular member 50 and the stylet 60, a sheath 70 are set so as to be located on the most proximal end side within their respective movable ranges (refer to FIG. 2). Additionally, a user starts the procedure in a state (refer to FIG. 6) where only the coupling support 23 is fixed to the operating part 3 of the endoscope 2 in advance by the slip-out stopper pin 25.

First, Step S1 of inserting the endoscope 2 into a patient's body, and observing a target to be treated is performed. FIG. 15 is an explanatory view for describing Step S1, showing one process of a procedure before the implant placement device 1 is used. In Step S1, as shown in FIG. 15, the insertion part 4 of the endoscope 2 is inserted from a patient's mouth in a state where the insertion part 30 of the applicator 20 is not inserted. The endoscope 2 is inserted into the duodenum Dd that is an upper alimentary canal. The condition outside the duodenum Dd is investigated by the ultrasonic observation part 5, and a user determines a place suitable for forming a through hole near the common bile duct Cb on the stomach St side rather than the duodenal papilla Dp. If the suitable place for forming the through hole is determined, Step S1 is ended and the process proceeds to Step S2.

Step S2 is the step of attaching the implant placement device 1 to the endoscope 2. In Step S2, the user inserts the insertion part 30 of the applicator 20 shown in FIG. 1 into the forceps channel 7 of the endoscope 2 shown in FIG. 6, and screws the attachment part 21 shown in FIG. 1 into the port 8 of the forceps channel 7 shown in FIG. 6, and engages each other. Moreover, as shown in FIG. 14, the coupling support 23 and the sheath slider 104 are fixed by the stopper portion 26. In this state, then applicator 20 does not come off from the endoscope 2 even if the endoscope 2 is gripped without touching then applicator 20. As shown in FIG. 14, in the positional relationship in which the attachment part 21 and the port 8 engage with each other, the distal end of the insertion part 30 protrudes from the distal end 4A of the insertion part 4 of the endoscope 2. If the implant placement device 1 is attached to the endoscope 2, Step S2 is ended and the process proceeds to Step S3.

Figure 16:
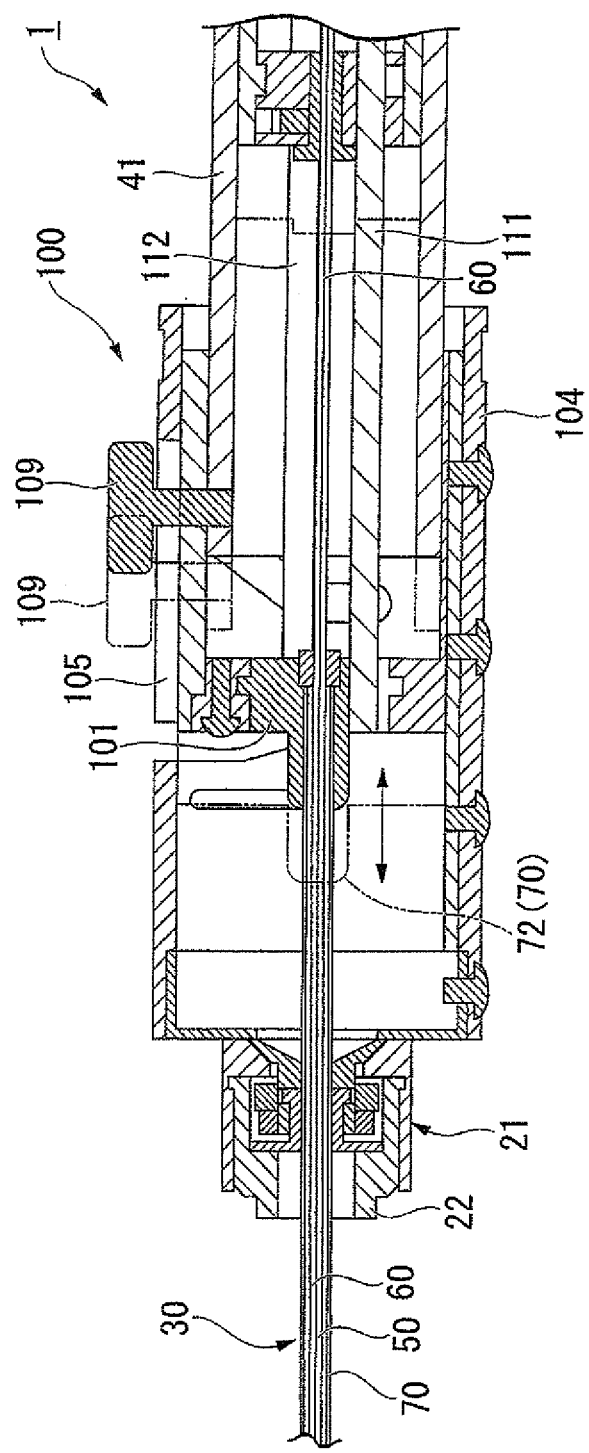
FIG. 16 is an operation explanatory view showing the operation of the sheath operating part when the implant placement device is used.
Figure 17:
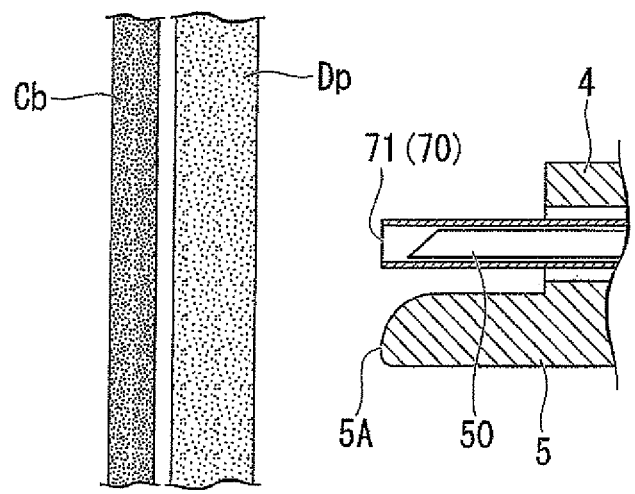
FIG. 17 is an operation explanatory view for describing the operation on the distal end side of the insertion part of the endoscope when the implant placement device is used.

Step S3 is the step of adjusting the position of the insertion part 30 with respect to the endoscope 2. FIG. 16 is an operation explanatory view showing the operation of the sheath operating part 100 of the implant placement device 1 in Step S3. Additionally, FIG. 17 is an operation explanatory view for describing the operation of Step S3 on the distal end side of the insertion part 4 of the endoscope 2 when the implant placement device 1 is used.

In Step S3, as shown in FIG. 16, first, the user loosens the sheath stopper 109 provided at the sheath operating part 100. Thereby, the sheath slider 104 and the operating body 41 are enabled to move relatively in the longitudinal direction of the operating body 41. The user advances and retreats the operating body 41 with respect to the sheath slider 104, and makes an adjustment such that the distal end of the sheath 70 is at an a suitable predetermined position with respect to the distal end 5A of the ultrasonic observation part 5. In the present embodiment, the above-described predetermined position in Step S3 is a position where the position of the distal end 5A of the ultrasonic observation part 5 and the position of the distal end 71 of the sheath 70 coincide with each other as shown in FIG. 17.

When the operating body 41 is moved to advance and retreat with respect to the sheath slider 104, the tubular member operating part 80 and the stylet operating part 90 that are coupled to the operating body 41 are integrally moved to advance and retreat along with the sheath 70, and thereby, the tubular member 50 and the stylet 60 are integrally moved to advance and retreat. For this reason, the relative positional relationship between the tubular member 50, the stylet 60, and the sheath 70 does not change. If the position of the insertion part 30 is adjusted to the above-described predetermined position, the sheath stopper 109 is fastened to fix the sheath slider 104 and the operating body 41, and Step S3 is ended and the process proceeds to Step S4.

Figure 18:
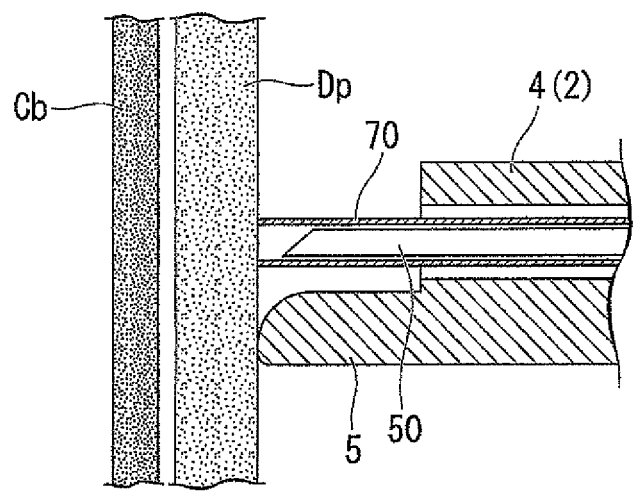
FIG. 18 is an operation explanatory view for describing the operation on the distal end side of the insertion part of the endoscope when the implant placement device is used.

Step S4 is the step of determining the part where a puncture is made with the tubular member 50. FIG. 18 is an operation explanatory view for describing the operation on the distal end side of the insertion part 4 of the endoscope 2 when the implant placement device 1 is used.

In Step S4, as shown in FIG. 18, the user performs scanning of the common bile duct Cb using the ultrasonic observation part 5 provided at the endoscope 2 over the duodenum Dd, and determines the position where the tubular member 50 is inserted into the duodenum Dd and the common bile duct Cb. If the position where a puncture is made with the tubular member 50 is determined, Step S4 is ended and the process proceeds to Step S5.

Figure 19A:
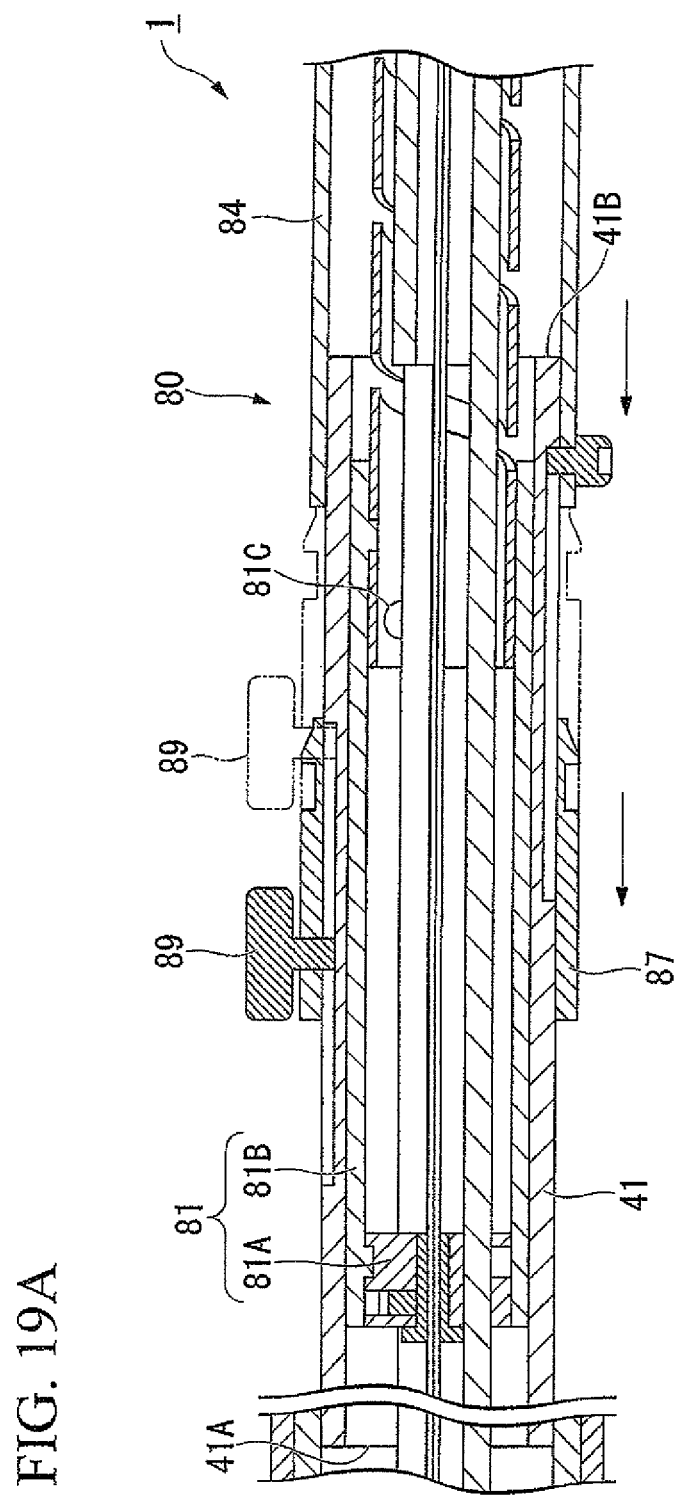
FIG. 19A is an operation explanatory view for describing the operation of the tubular member operating part when the implant placement device is used.
Figure 19B:
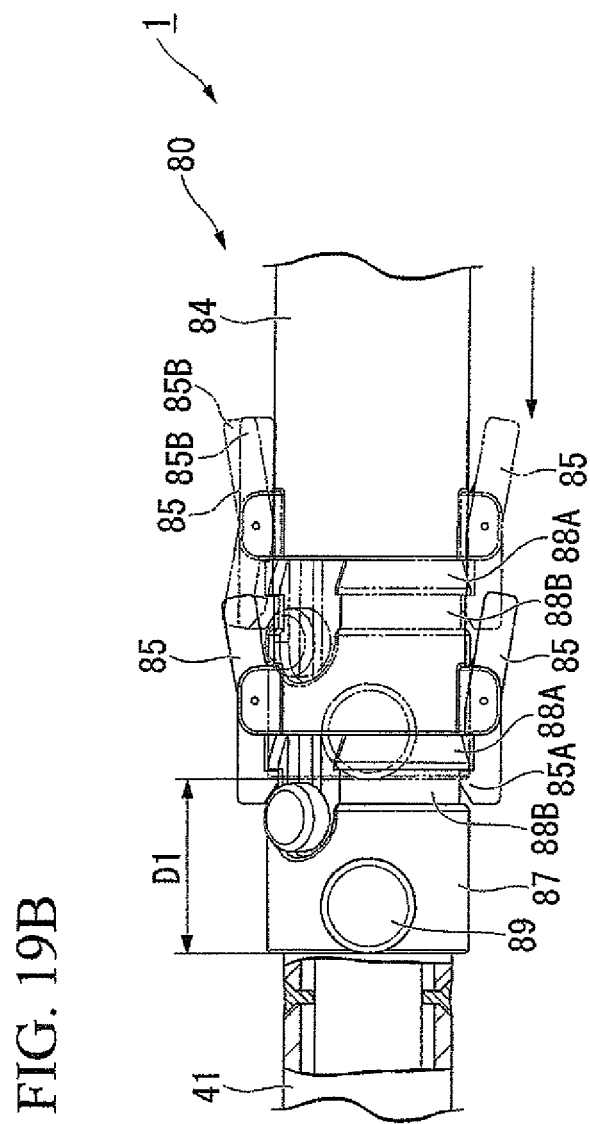
FIG. 19B is an operation explanatory view for describing the operation of the tubular member operating part when the implant placement device is used.
Figure 20:
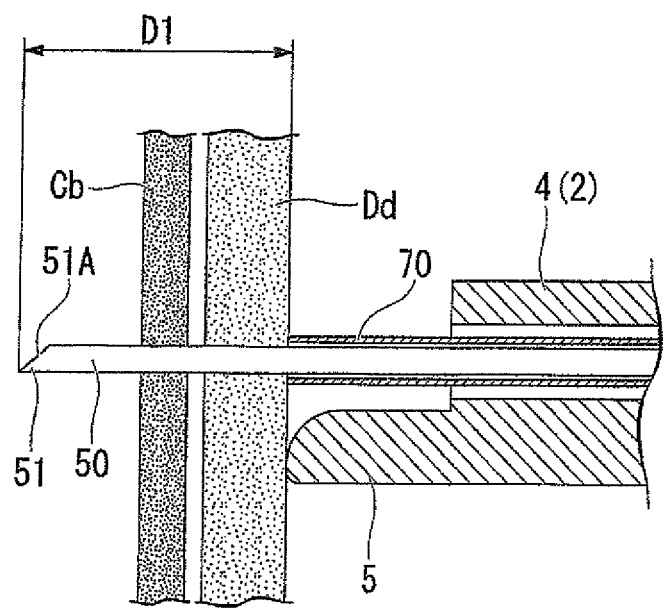
FIG. 20 is an operation explanatory view for describing the operation on the distal end side of the insertion part of the endoscope when the implant placement device is used.

Step S5 is the step of setting the insertion amount for puncturing the duodenum Dd and common bile duct Cb with the tubular member 50. FIGS. 19A and 19B are operation explanatory views for describing the operation of the tubular member operating part 80 when the implant placement device 1 is used. Additionally, FIG. 20 is an operation explanatory view for describing the operation on the distal end side of the insertion part 4 of the endoscope 2 when the implant placement device 1 is used.

In Step S5, as shown in FIG. 19A, first, the user loosens the positioning screw 89 attached to the slide stopper 87 of the tubular member operating part 80. Moreover, as shown in FIG. 19B, the user pushes in the proximal ends 85B of the pair of hooks 85 attached to the tubular member slider 84 radially inward from the tubular member slider 84. Then, the distal ends 85A of the pair of hooks 85 are separated from the engaging groove 88B of the slide stopper 87, thereby enabling the tubular member slider 84 and the slide stopper 87 to move relatively, and allowing the slide stopper 87 to move to advance and retreat in the longitudinal direction of the operating body 41.

After the slide stopper 87 is moved to a desired position with respect to the operating body 41, the user fastens the positioning screw 89 to fix the slide stopper 87 to the operating body 41. The distance between the slide stopper 87 and the tubular member slider 84 at this time becomes the amount D1 of puncture by which the body tissue (the duodenum Dd and common bile duct Cb) are punctured with the tubular member 50. If the puncture amount by which a puncture is made with the tubular member 50 is set, Step S5 is ended and the process proceeds to Step S6.

Step S6 is the step of puncturing the duodenum Dd and common bile duct Cb with the tubular member 50. In Step S6, as shown in FIG. 19A, the user moves the tubular member slider 84 to the distal end 41A side of the operating body 41 with respect to the operating body 41. Then, as shown in FIG. 2, the tubular member slider 84 moves to the distal end 41A side of the operating body 41 integrally with the fixing portion 81 coupled to the tubular member slider 84 shown in FIG. 19A. Thereby, the tubular member 50 fixed to the fixing portion 81 moves linearly to the distal end 51 sides, and as shown in FIG. 20, the tubular member 50 punctures the duodenum Dd and the common bile duct Cb from the distal end 51.

The user moves the tubular member slider 84 with respect to the slide stopper 87 until the tubular member slider 84 abuts on the slide stopper 87. Then, as shown in FIG. 19B, the distal ends 85A of the pair of hooks 85 provided at the tubular member slider 84 ride over the taper portion 88A of the slide stopper 87, respectively, and are fitted to the engaging groove 88B. Since the slide stopper 87 is fixed to the operating body 41, when the tubular member slider 84 and the slide stopper 87 engage with each other, the tubular member slider 84 is also held in a fixed positional relationship with respect to the operating body 41. For this reason, the tubular member 50 that has punctured the duodenum Dd and the common bile duct Cb does not return to the proximal end 52 side, and slip-out of the tubular member 50 from a tissue is suppressed.

If the tubular member 50 has punctured the duodenum Dd and the common bile duct Cb, Step S6 is ended and the process proceeds to Step S7.

Figure 21:
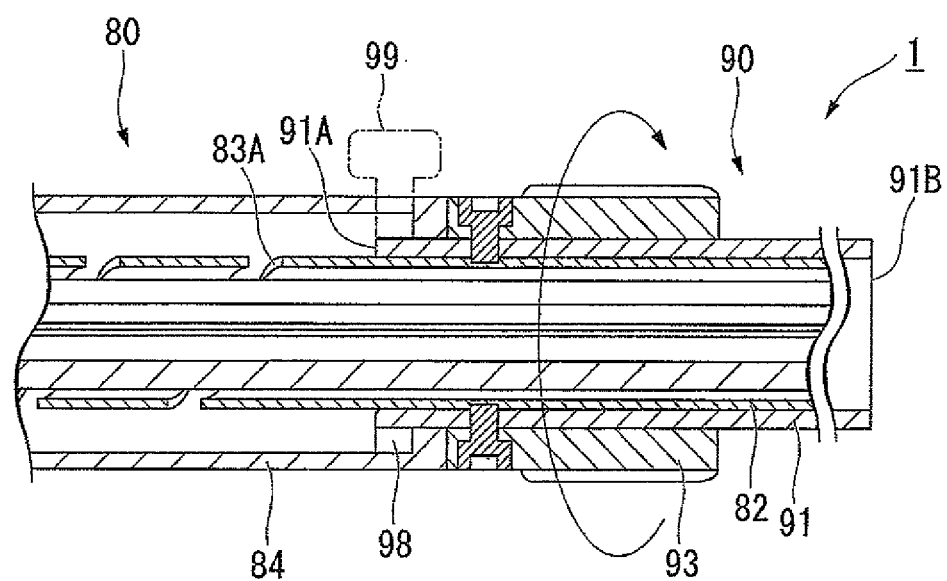
FIG. 21 is an operation explanatory view for describing the operation of the stylet operating part when the implant placement device is used.
Figure 22:
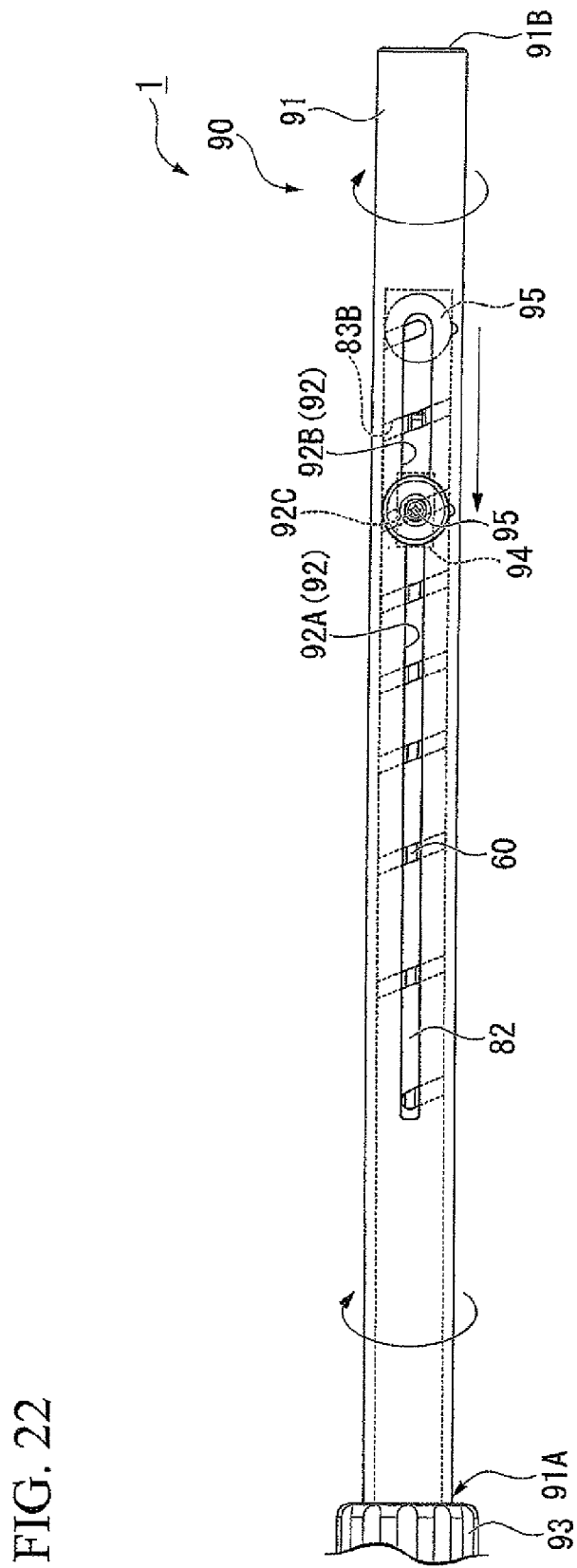
FIG. 22 is an operation explanatory view for describing the operation of the stylet operating part when the implant placement device is used.
Figure 23:
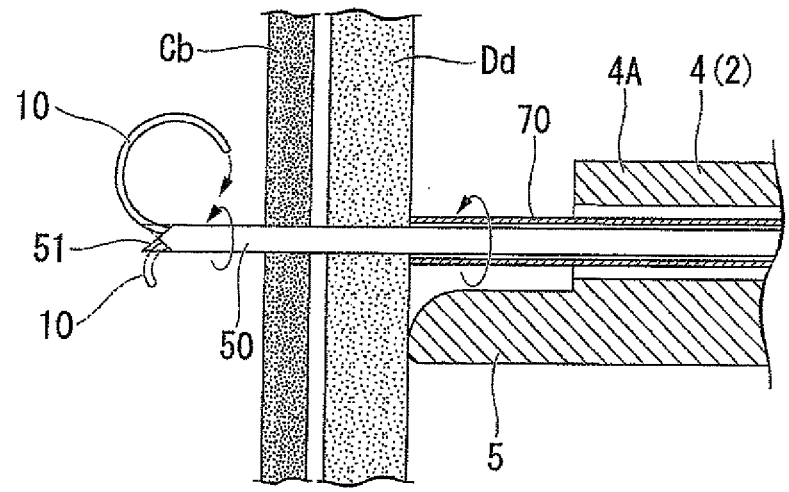
FIG. 23 is an operation explanatory view for describing the operation on the distal end side of the insertion part of the endoscope when the implant placement device is used.

Step S7 is a delivery step of delivering the tissue fastener 10 from the tubular member 50, and arranging a portion of the tissue fastener 10 to the common bile duct Cb side. FIGS. 21 and 22 are operation explanatory views for describing the operation of the stylet operating part 90 when the implant placement device 1 is used. Additionally, FIG. 23 is an operation explanatory view for describing the operation on the distal end side of the insertion part 4 of the endoscope 2 when the implant placement device 1 is used.

In Step S7, as shown in FIG. 21, the user removes the rotation regulating screw 99 attached to the tubular member slider 84. Thereby, the engagement between the tubular member slider 84 and the sheath tube 91 is released, so that the sheath tube 91 and the rotation input portion 93 can be rotated around an axis with respect to the tubular member slider 84.

The user grips the rotation input portion 93 and rotates the rotation input portion 93 with respect to the operating body 41. The rotational direction of the rotation input portion 93 is a direction that becomes the clockwise direction when the sheath tube 91 is seen from the proximal end 91B toward the distal end 91A, as shown by an arrow in FIG. 21. Then, the sheath tube 91 rotates around the axis of the sheath tube 91 with respect to the cam tube 82.

As shown in FIGS. 21 and 22, the guide pin 95 is inserted through the second spiral cam 83B of the cam tube 82 and the long hole 92 of the sheath tube 91, respectively. For this reason, the guide pin 95 moves to the distal end 91A side of the sheath tube 91 along the long hole 92 while being supported by the spiral cam 83. As a result, the fixing portion 94 to which the guide pin 95 is fixed also moves to the distal end 91A side of the sheath tube 91 integrally with the guide pin 95. Moreover, at this time, the guide pin 95 also rotates around the same axis as the sheath tube 91 as the sheath tube 91 rotates around an axis.

The stylet 60 moves to the distal end 51 side (refer to FIG. 2) of the tubular member 50 by the fixing portion 94 that moves to the distal end 91A side of the sheath tube 91. At this time, since the fixing portion 94 and the stylet 60 are fixed, the stylet 60 rotates integrally with the fixing portion 94.

Here, since the fixing portion 81, the fixing portion 94, and the fixing portion 101 are coupled together such that their rotations interlock with each other by the rotation interlocking mechanism 110 as shown in FIG. 13, both the fixing portion 81 and the fixing portion 101 rotate around an axis along with the fixing portion 94. For this reason, the tubular member 50 fixed to the fixing portion 81 and the sheath 70 fixed to the fixing portion 101 are rotated together so as to interlock with the rotational operation of the stylet 60. As a result, the stylet 60 moves to the distal end 51 side in the axial direction of the tubular member 50 inside the tubular member 50, while the circumferential relative position thereof has been a position positioned with respect to the tubular member 50.

Since the tubular member 50 and the stylet 60 rotates around an axis with respect to the operating body 41 on the distal end 4A side of the insertion part 4 of the endoscope 2, as shown in FIG. 23, the tissue fastener 10 is rotating around the axis of the tubular member 50 to the duodenum Dd and common bile duct Cb.

As shown in FIG. 22, when the fixing portion 94 moves to a boundary line 92C between the long hole 92A and the long hole 92B of the sheath tube 91, the second wall portion 95B of the guide pin 95 is caught in the long hole 92A. That is, since the guide pin 95 bites into the long hole 92 and the second spiral cam 83B, it is impossible for the user to rotate the sheath tube 91. In the present embodiment, since the long hole 92A has a length equivalent to two turns of the second spiral cam 83B of the cam tube 82, the metal wire rod of the tissue fastener 10 is paid out by two turns from the distal end 51 of the tubular member 50 when the sheath tube 91 cannot be rotated. The tissue fastener 10 is restored to a coiled form due to its own superelasticity in the portion paid out from the distal end 51 of the tubular member 50. Now, Step S7 is ended and the process proceeds to Step S8.

Figure 24:
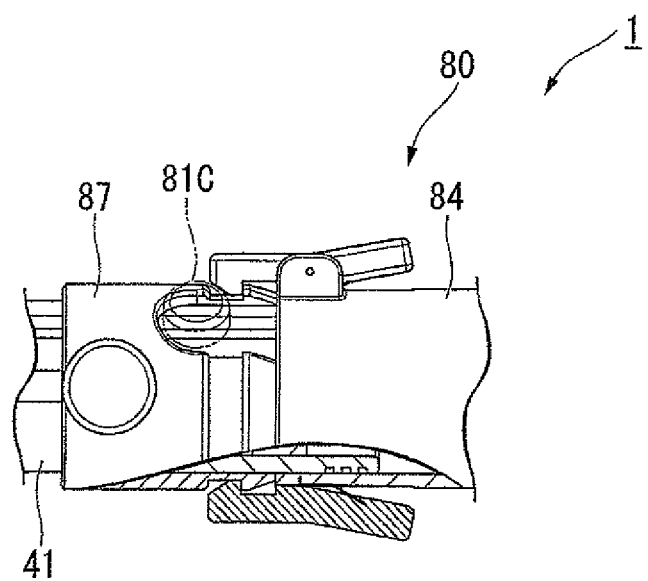
FIG. 24 is an operation explanatory view for describing the operation of the tubular member operating part when the implant placement device is used.
Figure 25:
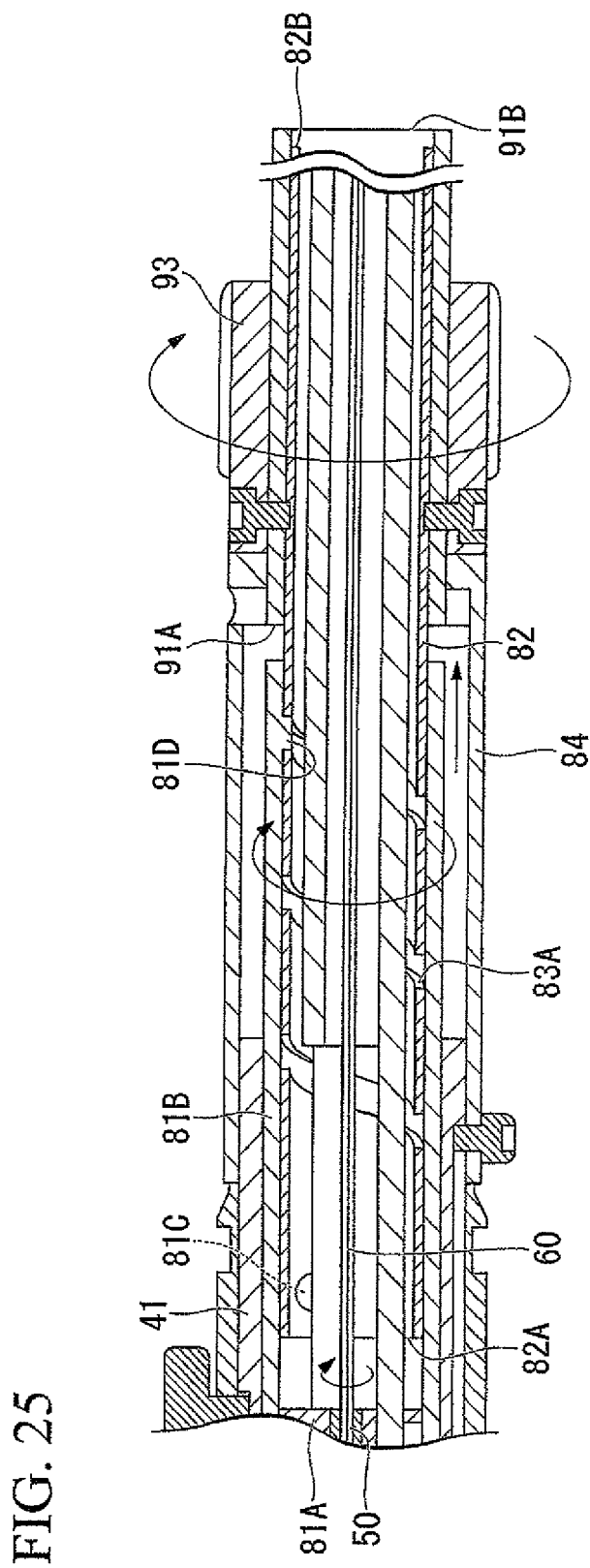
FIG. 25 is an operation explanatory view for describing the operation of the stylet operating part when the implant placement device is used.

Step S8 is an extraction step of extracting the tubular member 50 from the duodenum Dd and the common bile duct Cb in order to arrange the tissue fastener 10 on the duodenum Dd side. FIG. 24 is an operation explanatory view for describing the operation of the tubular member operating part 80 when the implant placement device 1 is used. Additionally, FIG. 25 is an operation explanatory view for describing the operation of the stylet operating part 90 when the implant placement device 1 is used. Additionally, FIG. 26 is an operation explanatory view for describing the operation on the distal end side of the insertion part 4 of the endoscope 2 when the implant placement device 1 is used.

In Step S8, as shown in FIG. 24, first, the user removes the fixing screw 81C attached to the operating body 41 between the tubular member slider 84 and the slide stopper 87. Then, as shown in FIG. 25, the fixation between the fixing portion 81 of the tubular member operating part 80 and the cam tube 82 is released, and the relative rotation between the fixing portion 81 and the can tube 82 around an axis becomes free. In this state, the user rotates the rotation input portion 93 with respect to the operating body 41 in the direction that becomes the clockwise direction when the sheath tube 91 is seen from the proximal end 91B toward the distal end 91A. Then, since the guide pin 95 catches the sheath tube 91 and the cam tube 82, the sheath tube and the cam tube do not relatively rotate, and the cam tube 82 rotates in the rotational direction of the rotation input portion 93 along with the sheath tube 91.

The cam tube 82 and the fixing portion 81 relatively rotate around an axis as the cam tube 82 rotates. More specifically, the fixing portion 81 does not rotate with respect to the operating body 41, but the cam tube 82 rotates with respect to the operating body 41. The pin 81D provided at the supporting member 81B of the fixing portion 81 slides along the first spiral cam 83A of the cam tube 82, and thereby, the supporting member 81B moves to the proximal end 82B side of the cam tube 82. Then, the fixing member 81A coupled to the supporting member 81B and the tubular member 50 fixed to the fixing member 81A also move to the proximal end 82B side of the cam tube 82 along with the supporting member 81B. At this time, since the fixing portion 94 of the stylet operating part 90 is caught in the boundary line 92C between the long hole 92A and the long hole 92B of the sheath tube 91, and is in a fixed state as shown in FIG. 22, the stylet 60 rotates around an axis without moving in the axial direction from the position of Step S7. For this reason, the tubular member 50 and the stylet 60 move relatively such that the tubular member 50 linearly moves to the proximal end 62 side of the stylet 60. As a result, the stylet 60 is pushed into the distal end 51 side of the tubular member 50.

Figure 26:
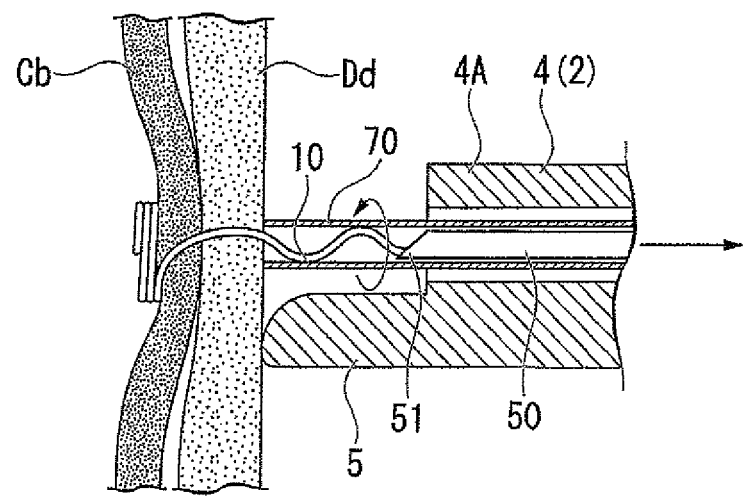
FIG. 26 is an operation explanatory view for describing the operation on the distal end side of the insertion part of the endoscope when the implant placement device is used.

On the distal end 4A side of the insertion part 4 of the endoscope 2, as shown in FIG. 26, due to the relative movement between the tubular member 50 and the stylet 60 caused by the linear movement of the above-described tubular member 50, a portion of tissue fastener 10 arranged at the common bile duct Cb is not pulled back to the duodenum Dd side, and the tubular member 50 is pulled out from the duodenum Dd and the common bile duct Cb, and is pulled into the inside of the sheath 70.

Here, since the supporting member 81B of the fixing portion 81 is supported by the operating body 41 so as to be movable to advance and retreat in the axial direction of the operating body 41 and be non-turnable, the fixing portion 81 cannot move to the proximal end side of the operating body 41 further in the place where the fixing portion 81 moved to the most proximal end side within a movable range inside the operating body 41. Thereby, the rotation input portion 93 is no longer rotated.

The user rotates the rotation input portion 93 until the rotation input portion 93 shown in FIG. 25 is no longer rotated. When the rotation input portion 93 cannot be rotated, the operation of pulling out the tubular member 50 is ended. Now, Step S8 is ended and the process proceeds to Step S9.

Step S9 is the step of bringing the duodenum Dd and the common bile duct Cb into close contact with each other, and relatively move the endoscope 2 and the duodenum Dd so as to obtain the positional relationship for optically observing the duodenum Dd side. That is, Step S9 is a pressing step of pressing the duodenum Dd in the insertion direction of the tubular member 50. Up to Step S8, the common bile duct Cb side is observed via the duodenum Dd by the observation using the ultrasonic observation part 5. However, after Step S9, a treatment on the duodenum Dd side is performed while observing the duodenum Dd side by the optical observation that allows a state to be more intuitively grasped.

Figure 27:
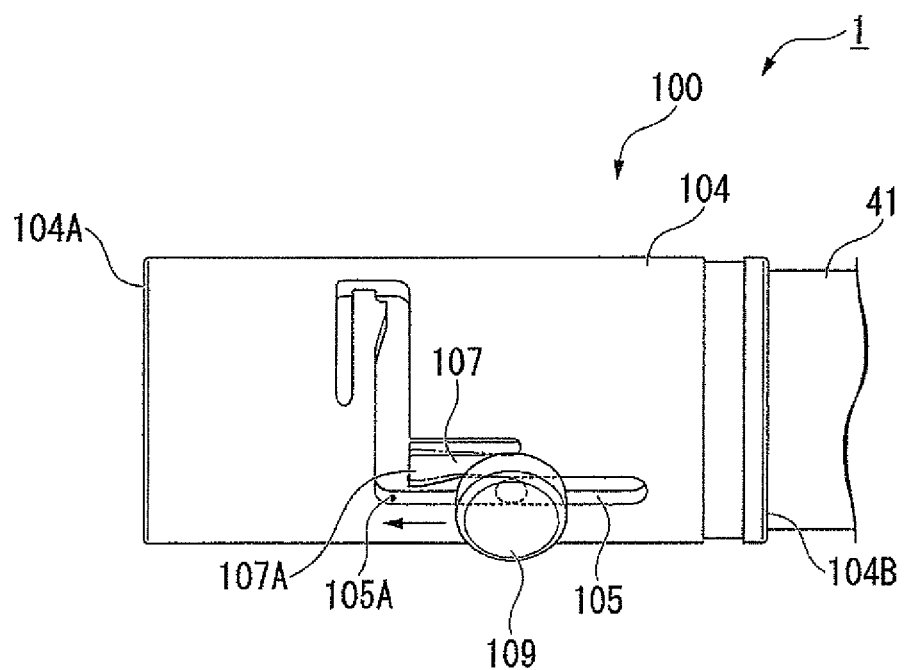
FIG. 27 is an operation explanatory view for describing the operation of the sheath operating part when the implant placement device is used.

FIG. 27 is an operation explanatory view for describing the operation of the sheath operating part 100 when the implant placement device 1 is used. Additionally, FIG. 28 is an operation explanatory view for describing the operation on the distal end side of the insertion part 4 of the endoscope 2 when the implant placement device 1 is used.

In Step S9, as shown in FIG. 27, the user loosens the sheath stopper 109 provided so as to protrude from the sheath slider 104 again. Thereby, similarly to the operation in Step S3, the tubular member 50, the stylet 60, and the sheath 70 are integrated, and are allowed to advance and retreat with respect to the insertion part 4 of the endoscope 2. The user pushes in the operating body 41 in the direction of the distal end 104A of the sheath slider 104. When the threaded portion 109A of the sheath stopper 109 rides over the projection 107A, and the sheath stopper 109 arrives at the end 105A of the cam groove 105, the return of the sheath stopper 109 to the sheath slider 104 is suppressed by the elastic stopper 107.

Figure 28:
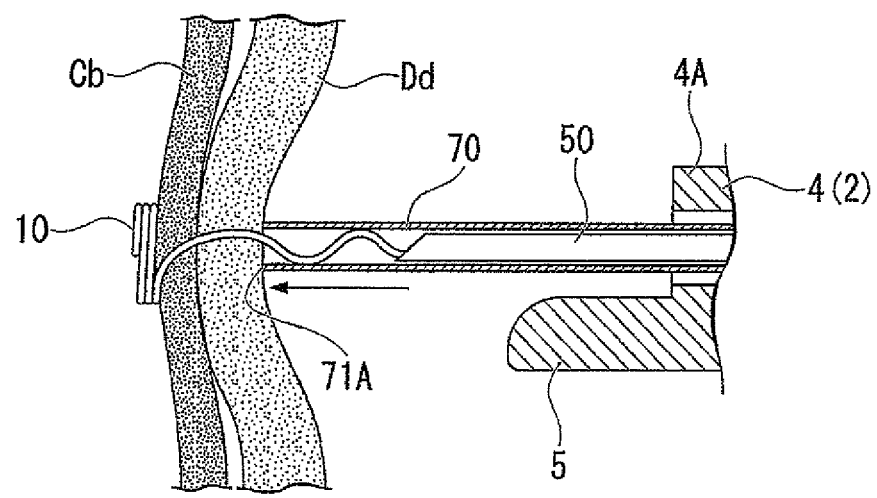
FIG. 28 is an operation explanatory view for describing the operation on the distal end side of the insertion part of the endoscope when the implant placement device is used.

As shown in FIG. 28, on the distal end 4A side of the insertion part 4 of the endoscope 2, the sheath 70 moves so as to be pushed out to the distal end 71 side further from a state where the sheath 70 abuts on the duodenum Dd. For this reason, the duodenum Dd is dented around the portion on which the sheath 70 abuts, the duodenum Dd is pressed in the direction of the common bile duct Cb, and the duodenum Dd and the common bile duct Cb are brought into close contact with each other. Additionally, the distal end 4A the insertion part 4 of the endoscope 2 and the duodenum Dd are separated from each other by pushing out the sheath 70 to the duodenum Dd side. Thereby, the endoscope 2 and the duodenum Dd move relatively, and a gap that allows the duodenum Dd to be observed is formed between the endoscope 2 and the duodenum Dd by to the optical observation mechanism provided at the insertion part 4 of the endoscope 2. Now, Step S9 is ended and the process proceeds to Step S10.

Figure 29:
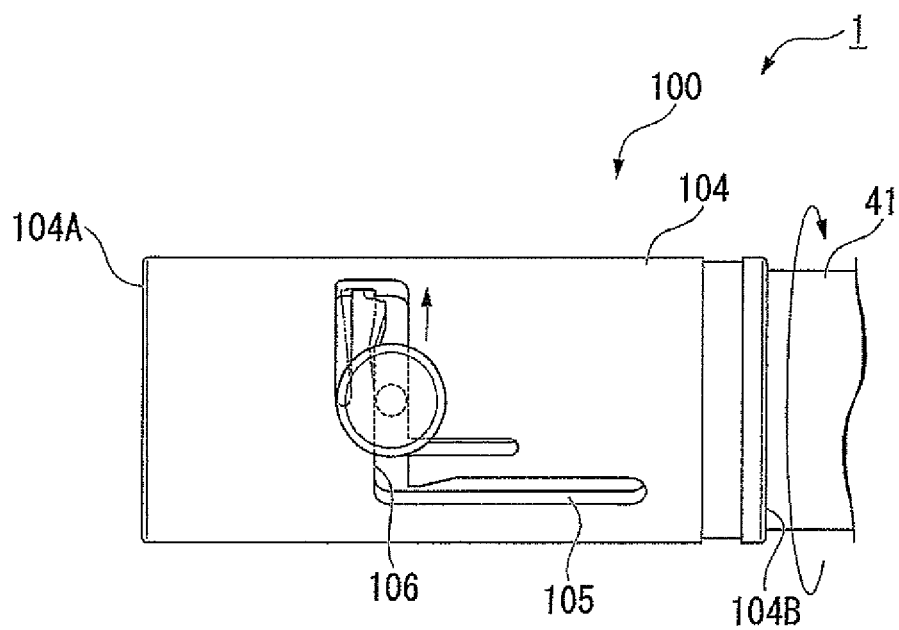
FIG. 29 is an operation explanatory view for describing the operation of the sheath operating part when the implant placement device is used.
Figure 30:
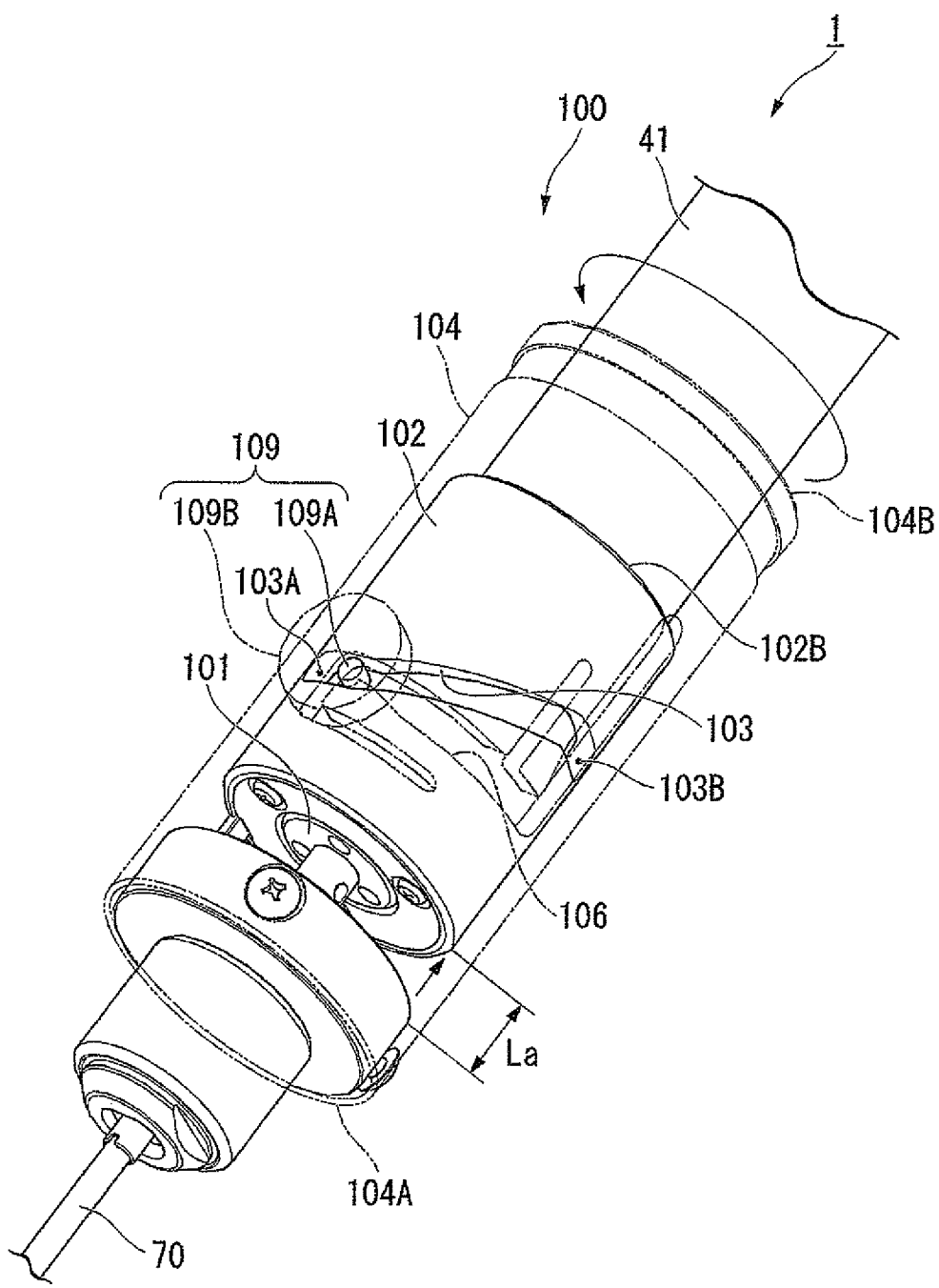
FIG. 30 is an operation explanatory view for describing the operation of the sheath operating part when the implant placement device is used.
Figure 31:
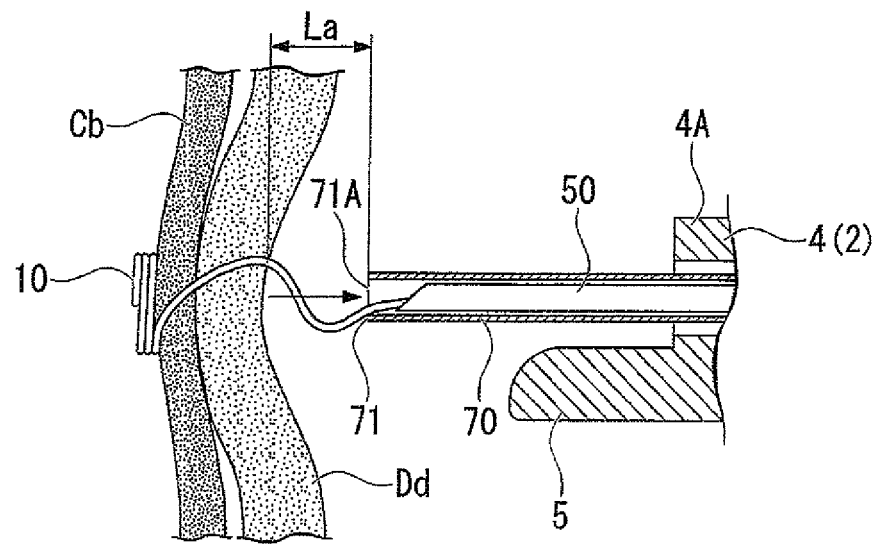
FIG. 31 is an operation explanatory view for describing the operation of the sheath operating part when the implant placement device is used.

Step S10 is an exposure step of arranging to expose the tissue fastener 10 to the duodenum Dd side. FIGS. 29 and 30 are operation explanatory views for describing the operation of the sheath operating part 100 when the implant placement device 1 is used. Additionally, FIG. 31 is an operation explanatory view for describing the operation of the sheath operating part 100 when the implant placement device 1 is used.

In Step S10, as shown in FIG. 29, the user does relatively turns the sheath slider 104 and the operating body 41 such that the operating body 41 is turned in the clockwise direction with respect to the sheath slider 104, as seen from the proximal end 104B side of the sheath slider 104 to the distal end 104A side. Since the sheath slider 104 is fixed to the operating part 3 of the endoscope 2 as shown in FIG. 14, in other words, the operating body 41 is turned with respect to the endoscope 2 and the sheath slider 104 in Step S10.

Then, the sheath stopper 109 moves relative to the sheath slider 104 along the cam groove 106 as shown in FIG. 30, and simultaneously, moves relative to the cam tube 102 through the inside of the tilt cam groove 103 of the cam tube 102. At this time, the sheath stopper 109 slides on the inner wall portion of the tilt cam groove 103, and moves the cam tube 102 to the proximal end 102B side by a length La. Since the cam tube 102 is coupled to the fixing portion 101 and the advance/retreat operation of the operating body 41 in the longitudinal axis interlocks with the cam tube 102 and the fixing portion 101, when the cam tube 102 moves to the proximal end 102B side, and thereby moves such that the fixing portion 101 and the sheath 70 fixed to the fixing portion 101 are pulled back to the proximal end 102E side of the cam tube 102. At this time, the tubular member 50 and the stylet 60 do not perform an advance/retreat operation from the position in Step S9.

As shown in FIG. 30, the user turns the operating body 41 with respect to the sheath slider 104. Then, the sheath stopper 109 moves relatively along the cam groove 106 up to the end of the cam groove 106 far from the cam groove 105. At this time, the sheath stopper 109 proceeds to ride over the projection 108A of the elastic stopper 108, and the return thereof to the cam groove 105 side is suppressed by the elastic stopper 108.

Since the sheath tube 91 and the fixing portion 94 are in a fixed state as shown in FIG. 22 by the operation of turning the operating body 41 around an axis with respect to the sheath slider 104, the fixing portion 94 and the stylet 60 fixed to the fixing portion 94 are turned around an axis. Since the turning operation of the fixing portion 94 is transmitted to the tubular member 50 and the sheath 70, respectively, by the rotation interlocking mechanism 110, the tubular member 50, the stylet 60, and the sheath 70 turn integrally.

As shown in FIG. 31, since the duodenum Dd is supported by the metal wire rod of the tissue fastener 10 on the distal end 4A side of the insertion part 4 of the endoscope 2, the above-described dented shape is maintained in the duodenum Dd. As the sheath 70 is pulled back in a state the above-described dented shape is maintained in the duodenum Dd, the duodenum Dd and the sheath 70 can be separated from each other by a length La.

Additionally, the sheath 70 is relatively moved to the proximal end 72 side with respect to the tubular member 50 and the stylet 60. For this reason, the metal wire rod of the tissue fastener 10 located inside the sheath 70 moves relatively so as to be paid out the distal end 71 of the sheath 70. The tissue fastener 10 paid out from the distal end 71 of the sheath 70 is restored to a coiled form due to its own superelasticity sequentially from the portion protruding from the sheath 70.

In order for the metal wire rod of the tissue fastener 10 to be restored to a coiled form, it is important to restore the shape of the metal wire rod gradually from the portion near the duodenum Dd. In the present embodiment, the length by which the sheath 70 is pulled back to the proximal end 72 side is the length La set by the shape of the tilt cam groove 103, and this length La is shorter than the length of one turn of the basic loop L1 of the tissue fastener 10. For this reason, when the sheath 70 is pulled back in Step S10, the metal wire rod of the tissue fastener 10 cannot form a new loop. Instead, the portion of the metal wire rod of the tissue fastener 10 that protrudes from the sheath 70 has a curved shape so as to form a portion of the loop shape. Additionally, by integrally turning the tubular member 50, the stylet 60, and the sheath 70, the tissue fastener 10 is laid down so as to run along the duodenum Dd, that is, the metal wire rod of the tissue fastener 10 can be tilted and made to run along the duodenum Dd. Thereby, a curved shape serving as a trigger for being restored to a loop shape without entanglement of the metal wire rod of the tissue fastener 10 is formed on the duodenum Dd side. Now, Step S10 is ended and the process proceeds to Step S11.

Step S11 is the step of cutting off the tissue fastener 10 from the applicator 20.

Figure 32:
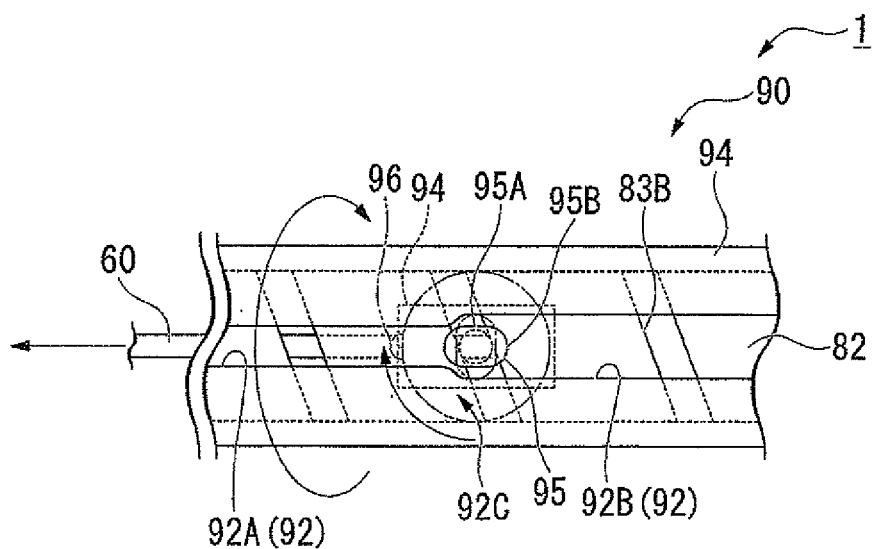
FIG. 32 is an operation explanatory view for describing the operation of the stylet operating part when the implant placement device is used.
Figure 33:
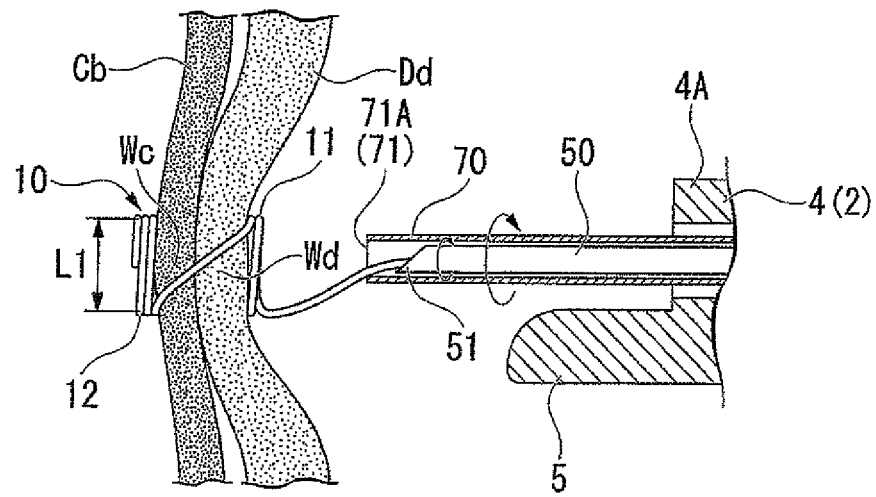
FIG. 33 is an operation explanatory view for describing the operation on the distal end side of the insertion part of the endoscope when the implant placement device is used.
Figure 34:
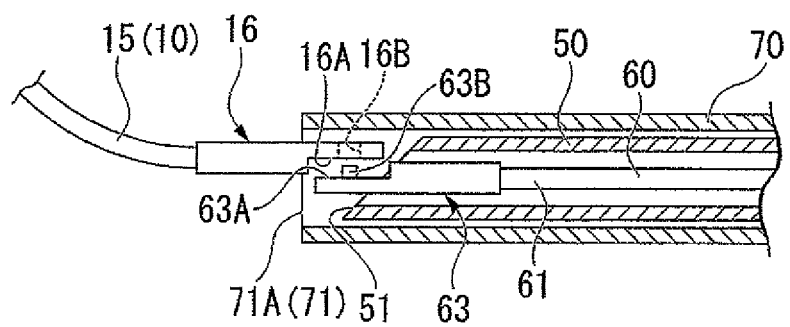
FIG. 34 is an operation explanatory view for describing the operation on the distal end side of the insertion part of the endoscope when the implant placement device is used.

In the above-described Step S10, the metal wire rod of the tissue fastener 10 is exposed to the duodenum Dd side. Subsequently to this, the metal wire rod is further paid out to the distal end 51 side from the tubular member 50 in Step S11. FIG. 32 is an operation explanatory view for describing the operation of the stylet operating part 90 when the implant placement device 1 is used. Additionally, FIG. 33 is an operation explanatory view for describing the operation on the distal end side of the insertion part 4 of the endoscope 2 when the implant placement device 1 is used. Additionally, FIG. 34 is an operation explanatory view for describing the operation on the distal end side of the insertion part 4 of the endoscope 2 when the implant placement device 1 is used.

First, as shown in FIG. 32, the user turns the guide pin 95 located at the boundary line 92C between the long holes 92A and 92B of the sheath tube 91 of the stylet operating part 90 around the axis of the guide pin 95 by 90 degrees. Then, the first wall portion 95A of the guide pin 95 is directed to the width direction of the long hole 92, so that the guide pin 95 can enter the long hole 92A.

Subsequently, similarly to the operation in Step S7, the user rotates the rotation input portion 93 with respect to the operating body 41 in the direction that becomes the clockwise direction when the operating body 41 is seen from the proximal end 41B toward the distal end 41A (refer to FIGS. 21 and 22). At this time, since the first spiral cam 83A of the cam tube 82 engages with the fixing portion 81 of the tubular member operating part 80, the cam tube 82 and the fixing portion 81 do not turn relatively, and the cam tube 82 moves relative to the sheath tube 91 around an axis similarly to Step S7. For this reason, as shown in FIG. 32, the fixing portion 94 fixed to the guide pin 95 runs along the second spiral cam 83B of the cam tube 82, and relatively moves to the distal end 91A side of the sheath tube 91 while rotating around the axis of the sheath tube 91 along the long hole 92A of the sheath tube 91.

Then, the stylet 60 fixed to the fixing portion 94 rotates integrally with the fixing portion 94, and moves to the distal end 91A side of the sheath tube 91. Thereby, the stylet 60 pushes out the tissue fastener 10 to the distal end 51 side of the tubular member 50 inside the tubular member 50. Moreover, when the fixing portion 94 rotates, the tubular member 50, the stylet 60, and the sheath 70 rotate integrally such that the rotational operations thereof around an axis interlock with each other by the rotation interlocking mechanism 110 coupled to the fixing portion 94.

As shown in FIG. 33, the tissue fastener 10 paid out from the distal end 51 of the tubular member 50 by the stylet 60 is restored to a coiled form due to its own superelasticity on the duodenum Dd side. As shown in FIG. 34, when the coupling portion 63 provided at the distal end 61 of the stylet 60 comes out from the distal end 51 of the tubular member 50, the coupling portion 16 supported by the inner wall of the tubular member 50 is no longer supported by the inner wall of the tubular member 50. Then, the through hole 16B of the coupling portion 16 come off from the projection 63B of the coupling portion 63. Thereby, the tissue fastener 10 is cut off from an applicator 20, and the tissue fastener 10 is placed in the body.

If the tissue fastener 10 is placed in the body, the stopper portion 26 of the coupling support 23 attached to the operating part 3 of the endoscope 2 shown in FIG. 14 is removed, and the implant placement device 1 is removed from the endoscope 2. Moreover, the insertion part 4 of the endoscope 2 is extracted from the inside of a patient's body. Now, a series of procedures that place the implant (tissue fastener 10) in the body are ended.

After the tissue fastener 10 is placed, the intestinal wall Wd of the duodenum Dd and the duct wall Wc of the common bile duct Cb that are located within the basic loop L1 of the tissue fastener 10 are fastened by the first tissue fixing section 11 and the second tissue fixing section 12 (refer to FIG. 33). Thereby, in the duodenum Dd and the common bile duct Cb, a blood flow is interrupted and the portion within the basic loop L1 causes a pressure necrosis. Moreover, the intestinal wall Wd and the duct wall Wc coalesce and join together around the basic loop L1.

The necrotized tissue and the tissue fastener 10 fall off from a placement position where the tissue fastener 10 is placed. At this time, the first tissue fixing section 11 and the second tissue fixing section 12 are always biased to the inner cavity side of the duodenum Dd by the outer peripheral spring portion 13. For this reason, when the tissue fastener 10 falls off from other tissues, the tissue fastener reliably fall off to the inner cavity side of the duodenum Dd. The tissue fastener 10 that has fallen off to the inner cavity of the duodenum Dd is excreted to the outside of the body through the small intestine and the large intestine. At this time, since the coupling portion 16 extends toward the inward direction of the loop of the tissue fastener 10, there is no case that the coupling portion 16 contacts a tissue and damages the tissue when the tissue fastener 10 moves within an alimentary canal.

As the tubular member and the sheath are configured to rotate relatively, the inner wall of the sheath may be shaved off by the distal end of the tubular member that is sharply formed. The shavings of the sheath generated at this time may be scattered within a body, such as the inside of the duodenum or the inside of the common bile duct, and the foreign matter that is not meant may be left within the body. In contrast, in the implant placement device 1 of the present embodiment, the rotational operations of the tubular member 50, the stylet 60, and the sheath 70 always interlock with each other by the rotation interlocking mechanism 110. As the rotational operations of the tubular member 50 and a sheath 70 interlocks with each other by the rotation interlocking mechanism 110, the tubular member 50 and a sheath 70 rotate integrally, and the circumferential relative positions of the tubular member 50 and a sheath 70 has a fixed relationship. For this reason, generation of the shavings of the sheath 70 can be suppressed by reducing such an operation that the distal end 51 of the tubular member 50 shaves off the inner wall of the sheath 70.

Additionally, the three-layer coil sheath 53 is provided on the external surface of the tubular member 50 so as to be interposed between the tubular member 50 and the sheath 70. In the present embodiment, the three-layer coil sheath 53 is formed from a three-layer coil. Thus, the insertion part 30 can be flexibly bent inside the forceps channel 7, and the rotation following capability of the insertion part 30 when the user operates the applicator 20 and rotates the insertion part 30 is high. Thereby, the operation that the user operates the applicator 20 on the endoscope 2 side can be transmitted to the distal end side of the insertion part 30 with high precision.

Additionally, the stylet 60 is formed from a material having superelasticity. Thus, the insertion part 30 can be flexibly bent inside the forceps channel 7, and the rotation following capability of the insertion part 30 when the user operates the applicator 20 and rotates the insertion part 30 is high.

Additionally, the sheath operating part 100 is provided with the sheath slider 104 formed with the cam groove 105 and the cam groove 106, and the cam tube 102 formed with the tilt cam groove 103. Thus, the operation that ejects the sheath 70 to the duodenum Dd side, and operation that pulls back the sheath 70 by a length shorter than the length of one turn of the basic loop L1 of the tissue fastener 10 can be continuously performed in this order. At this time, the amount by which the sheath 70 is ejected is determined by the length of the cam groove 105, and the amount by which the sheath 70 is pulled back is determined by the distance between the end 103A and ends 103B of the tilt cam groove 103 when the cam tube 102 is seen in the longitudinal direction. For this reason, the sheath 70 can be simply and accurately advanced and retreated. As a result, the tissue fastener 10 can be reliably arranged on the duodenum Dd side.

Additionally, in a state where the sheath 70 is pulled back to the proximal end 72 side after the sheath 70 is ejected to the distal end 71 side, the sheath 70 protrudes longer than the external diameter of the third loop L3 of the tissue fastener 10 to the distal end 71 side from the distal end (protruding end) 5A of the ultrasonic observation part 5 provided at the insertion part 4 of the endoscope 2. For this reason, even if the tissue fastener 10 is unintentionally moved in the operation of placing the tissue fastener 10 on the duodenum Dd side, collision of the tissue fastener 10 with the endoscope can be suppressed.

Additionally, since the tubular member 50, the stylet 60, and the sheath 70 linearly operate integrally when the operating body 41 is linearly moved along the cam groove 105 of the sheath slider 104, the duodenum Dd and the common bile duct Cb are not fastened by the tissue fastener 10 and the sheath 70. For this reason, invasion into a body tissue in the midst of the procedure of placing the tissue fastener 10 can be reduced. Moreover, since the tubular member 50 functions as a core inside the sheath 70, deflection of the sheath 70 can be reduced. As a result, wobbling of the duodenum Dd pressed by the sheath 70 can be reduced, and observation by the optical observation mechanism becomes easy.

Additionally, since the sheath slider 104 is formed with the elastic stopper 107, the position of a sheath 70 can be maintained against the force with which the sheath 70 is pushed back by the tissue after the sheath 70 is ejected to the distal end 71 side. For this reason, even if the user lifts his/her hand from the applicator 20, the ejection amount of the sheath 70 can be maintained.

Additionally, since the sheath slider 104 is formed with the elastic stopper 108, the pull-back amount of the sheath 70 can be maintained even if the user lifts his/her hand from the applicator 20 after the sheath 70 is pulled back to the proximal end 72 side.

Additionally, when the sheath 70 is pulled back by the sheath slider 104 and the cam tube 102, the operating body 41, and the stylet 60 and the tubular member 50 whose rotation follows the operating body 41 rotate integrally. For this reason, even if the tissue fastener 10 is paid out from the distal end 71 of the sheath 70, entanglement of the metal wire rod of the tissue fastener 10 can be suppressed.

Additionally, the cam tube 82 and the cam tube 102 are formed with the cams (the second spiral cam 83B and the tilt cam groove 103) such that the winding direction of the tissue fastener 10 is a counterclockwise direction, whereas the direction in which the tubular member 50, the stylet 60, and the sheath 70 are rotated becomes the clockwise direction as seen from the proximal end 52 of the tubular member 50 toward the distal end 51 thereof. For this reason, even if the tissue fastener 10 is paid out from the distal end 51 of the tubular member 50, entanglement of the metal wire rod of the tissue fastener 10 can be suppressed. In addition, in a case where the tissue fastener 10 is wound clockwise, it is preferable that the direction in which the tubular member 50, the stylet 60, and the sheath 70 are rotated be the counterclockwise direction as seen from the proximal end 52 of the tubular member 50 toward the distal end 51 thereof. This can be easily design-changed by changing the shape of the cams of the cam tubes 82 and 102 and the shape of the cam of the sheath slider 104.

Additionally, since the tubular member slider 84 of the tubular member operating part 80 is provided with the pair of hooks 85, and the slide stopper 87 is formed with the engaging groove 88B that engaged with the hook 85, unintentional advance/retreat of the tubular member slider 84 in the longitudinal direction of the operating body 41 can be suppressed after the step of puncturing a tissue with the tubular member 50 is completed.

Additionally, since the slide stopper 87 is formed with the taper portion 88A, the distal end 85A of the hook 85 rides over the taper portion 88A by the operation that presses the tubular member slider 84 against the slide stopper 87. For this reason, the tubular member slider 84 and the slide stopper 87 can be fixed only by pressing the tubular member slider 84 against the slide stopper 87.

Additionally, since the tubular member 50 is inserted into a tissue after the insertion amount of the tubular member 50 is set in advance by the slide stopper 87, the tubular member 50 is not inserted longer than needed, or the length by which the tubular member 50 is inserted does not run short. For this reason, the tubular member 50 can be reliably inserted through a tissue, and there is no possibility that other tissues may be damaged by the tubular member 50.

Since the coupling screw 81C that couples the supporting member 81B of the fixing portion 81 and the cam tube 82 together in an disengageable manner is provided, the advance/retreat operations of the tubular member 50 and the stylet 60 can be interlocked with each other when the coupling screw 81C is attached, and the tubular member 50 and the stylet 60 can be relatively moved by removing the coupling screw 81C. For this reason, when the tubular member 50 is pulled back to the proximal end 52 side, the stylet can be relatively moved to the distal end 51 side of the tubular member 50, and the tissue fastener 10 can be paid out from the distal end of the tubular member 50. For this reason, even if the tubular member 50 is pulled back, the first tissue fixing section 11 of the tissue fastener 10 can suppress the pressure on a body tissue on the common bile duct Cb side that the first tissue fixing section 11 contacts, without being pulled to the duodenum Dd side.

Additionally, since the tubular member 50 can be pulled back until the fixing portion 81 is moved by the first spiral cam 83A and the distal end 51 of the tubular member 50 fixed to the fixing portion 81 is located inside the sheath 70, the sharp distal end 51 is not exposed to the outside after the tubular member 50 is pulled back. For this reason, there is no possibility that other tissues may be damaged by the distal end 51 of the tubular member 50.

Additionally, according to the implant placing method of the present embodiment, the duodenum Dd is pressed against the common bile duct Cb side by moving the sheath 70 to the distal end 71 side in Step S9. Thus, the duodenum Dd and the common bile duct Cb can be brought into close contact with each other. For this reason, the duodenum Dd and the common bile duct Cb can be reliably coalesced after the tissue fastener 10 is placed.

Additionally, when the sheath 70 is ejected to the distal end 71 side in Step S9, the tubular member 50 and the stylet 60 protrudes to the distal end 71 side along with the sheath 70. For this reason, the position of the tissue fastener 10 relative to the sheath 70 does not change. Even if the sheath 70 is pushed against the duodenum Dd, there is no possibility that the duodenum Dd and the common bile duct Cb may be pinched by the tissue fastener 10 and the sheath 70.

Additionally, at this time, the tubular member 50 can reinforce the sheath 70 inside the sheath 70 such that the sheath 70 does not deflect, the duodenum Dd and the common bile duct Cb can be supported against the force with which the sheath 70 is pushed back from the duodenum Dd or the common bile duct Cb.

Additionally, after the sheath 70 is ejected to the distal end 71 side in Step S9, in Step S10, the sheath 70 is pulled back to the proximal end 72 side, and thereby, the metal wire rod of the tissue fastener 10 is exposed from the distal end 71 of the sheath 70. For this reason, the shape of the tissue fastener 10 can be gradually restored from the portion near the duodenum Dd on the duodenum Dd side by curving the metal wire rod of the tissue fastener 10 with elasticity on the duodenum Dd side so as to follow its own loop shape in the order exposed from the distal end of the sheath 70.

Additionally, when the pull-back amount of the sheath 70 is longer than one turn of the metal wire rod, there is a possibility that the metal wire rod may be restored to a coiled form at a position distant from the wall portion of the duodenum Dd, and form an unintended loop, and the tissue fastener 10 may be entangled. In the implant placing method of the present embodiment, the length by which the sheath 70 is pulled back to the proximal end 72 side is the length La and is shorter than the length of the metal wire rod equivalent to one circumferential turn of the basic loop L1 of the tissue fastener 10. Thus, an unintended new loop is not formed by the operation of pulling back the sheath 70.

Additionally, in Step S10, even after the sheath 70 is pulled back to the proximal end 72 side, the sheath 70 does not protrude from the distal end 4A of the insertion part 4 of the endoscope 2 equal to or more than the circumferential length of the third loop L3. For this reason, even if the tissue fastener 10 is unintentionally moved, collision of the tissue fastener 10 with the endoscope 2 can be suppressed.

Additionally, in Step S10, since the stylet 60 is turned inside the sheath 70 simultaneously when the operation of pulling back the sheath 70 to the proximal end 72 side is performed, the metal wire rod of the tissue fastener 10 exposed to the outside by pulling back the sheath 70 can be guided so as to follow a coiled form.

Although the preferable embodiments of the present invention have been described hitherto, the present invention is not limited to the embodiments. Additions, omissions, substitutions, and other modifications can be made without departing from the scope of the present invention.

For example, although the example in which the coil sheath 53 is a three-layer coil has been shown in the above-described embodiment, the effects of the present invention can be exhibited if the coil sheath 53 is a coil sheath of a plurality of layers more than two layers. In this regard, since the external diameter of the coil sheath increases if the layers of the coil sheath increases, it is preferable to select the external diameter of the insertion part and the number of the layers of the coil sheath so that the tissue fastener 10 can be received inside the coil sheath, and can be inserted through the forceps channel.

Additionally, the example in which the tubular member 50 is composed of a uniform metallic conduit has been shown in the above-described embodiment. However, the invention is not limited. Instead of the tubular member 50, a tubular member that has a distal end tubular portion that is formed substantially in a tubular shape, and a multilayer coil sheath fixed to the proximal end side of the distal end tubular portion can be employed. In this case, the tissue fastener 10 is arranged inside the distal end tubular portion, and the stylet 60 extends to the fixing portion 94 through the inside of the multilayer coil sheath. According to such a configuration, the rotation following capability of the tubular member and the flexibility of the tubular member can be further enhanced, respectively.

Additionally, instead of the tubular member 50 and the multilayer coil sheath, a tubular member that has the above-described distal end tubular portion, and an elastic tubular portion having superelasticity fixed to the proximal end side of the distal end tubular portion can be adopted. In this case, since the insertion part of the endoscope is intricately curved, even if the forceps channel is intricately curved similarly to the insertion part, plastic deformation of the tubular member can be suppressed, and the insertion part can be suitably rotated within the forceps channel. In addition, in this case, the distal end tubular portion may have superelasticity similarly to the elastic tubular portion, and all the portions of the tubular member may be integrally formed from a material having superelasticity. As an example of the material having superelasticity, for example, a nickel titanium alloy can be employed.

Additionally, instead of the tubular member 50 and the multilayer coil sheath, a tubular member that has the above-described distal end tubular portion, and a resin tubular portion made of resin fixed to the proximal end side of the distal end tubular portion can be adopted. In this case, since the insertion part of the endoscope is intricately curved, even if the forceps channel is intricately curved similarly to the insertion part, the resin tubular portion does not deform plastically. Thus, the insertion part can be suitably rotated within the forceps channel. In addition, in this case, the distal end tubular portion may be formed from resin similarly to the resin tubular portion. However, in a case where all the portions of the tubular member are made of resin, the distal end of the tubular member is formed especially sharply so that the tubular member can be inserted into a body tissue, or it is necessary to form a puncture in advance a body tissue by other treatment tools.

In addition, the present invention is not limited by the above description and is limited only by the scope of the appended claims.

The invention claimed is:

1. An ultrasonic endoscope treatment tool provided to be fixed to an ultrasonic endoscope to perform treatment on a body tissue the ultrasonic endoscope treatment tool comprising:
    an insertion part including:
        a sheath having a longitudinal axis; and
        a tubular member having an opening formed on a distal end side thereof, movable along the longitudinal axis, and provided with a lumen communicating with the opening; and
    a main body provided at a proximal side of the insertion part, the main body including:
        an operating part provided to be coupled to the sheath;
        a mounting part which is provided to be coupled to the operating part and to fix the ultrasonic endoscope treatment tool to the ultrasonic endoscope;
        a tubular member slider provided to advance and retract the tubular member in an axial direction of the tubular member with respect to the operating part;
        a slide stopper provided to move relative to the operating part in the axial direction of the tubular member and capable of being fixed to the operating part; and
        a coupling member provided to couple the tubular member slider with the slide stopper when the tubular member slider has come into contact with the slide stopper such that an advancement and a retraction of the tubular member slider with respect to the slide stopper are restricted,
    wherein
    the tubular member is capable of being introduced to the body tissue by being inserted through the inside of the sheath,
    the slide stopper is provided on a distal side of the tubular member slider in an insertion direction of the tubular member, and both the advancement and the retraction of the tubular member slider with respect to the operating part are restricted when the tubular member slider is coupled to the slide stopper in a state where the slider stopper is fixed to the operating part.

2. The ultrasonic endoscope treatment tool according to claim 1,
wherein the insertion part further includes a stylet provided within the lumen, the stylet being movable in the longitudinal axis direction within the lumen and rotatable around the longitudinal axis.

3. The ultrasonic endoscope treatment tool according to claim 2, wherein
the sheath is rotatable around the axial direction of the tubular member in a state where the tubular member is inserted through the sheath.

4. The according to claim 3, wherein
the stylet, the tubular member, and the sheath are rotatable integrally around the axis of the tubular member.

5. The ultrasonic endoscope treatment tool according to claim 2, wherein
the stylet is formed from a material having superelasticity.

6. The ultrasonic endoscope treatment tool according to claim 2, wherein
the ultrasonic endoscope treatment tool being provided to place an implant within the body tissue,
the implant has a coil-spring shape,
the implant is arranged in the tubular member in a stretched state when introduced to the body tissue,
and the ultrasonic endoscope treatment tool further includes a sheath operating part moving at least the sheath to the distal end side in the insertion direction, and moving at least the sheath to the proximal end side in the insertion direction.

7. The ultrasonic endoscope treatment tool according to claim 6, wherein
the sheath operating part moves the sheath relative to the stylet in a direction of the longitudinal axis of the sheath when the sheath is moved to the proximal end side in the insertion direction.

8. The ultrasonic endoscope treatment tool according to claim 6,
wherein a movement distance by which the sheath is moved to the proximal end side by the sheath operating part is set to be shorter than a length equivalent to one round of the coil of the implant.

9. The ultrasonic endoscope treatment tool according to claim 6,
wherein the distance by which the sheath protrudes from the distal end of the insertion part of the ultrasonic endoscope when the sheath is moved to the proximal end side in the insertion direction by the sheath operating part is greater than the size of the external diameter of the coil of the implant.

10. The ultrasonic endoscope treatment tool according to claim 6,
wherein the sheath operating part moves the stylet along with the sheath when moving the sheath to the distal end side in the insertion direction.

11. The ultrasonic endoscope treatment tool according to claim 10,
wherein the sheath operating part moves the tubular member and the stylet along with the sheath.

12. The ultrasonic endoscope treatment tool according to claim 6,
wherein the sheath operating part has a stopper that fixes the axial relative positions of the sheath and the sheath operating part at a predetermined movement distance when the sheath is moved to the distal end side in the insertion direction.

13. The ultrasonic endoscope treatment tool according to claim 6,
wherein the sheath operating part has a stopper that fixes the axial and circumferential relative positions of the sheath and the sheath operating part at a predetermined movement distance when the sheath is moved to the proximal end side in the insertion direction.

14. The ultrasonic endoscope treatment tool according to claim 6, wherein
the stylet is arranged inside the tubular member more proximal than the implant in an insertion direction of the tubular member, and the stylet is capable of being coupled to the implant,
the sheath is rotatable around the axial direction of the tubular member,
the operating part is coupled to the sheath operating part,
the ultrasonic endoscope treatment tool further includes a cam tube arranged coaxially with the central axis of the sheath operating part inside the sheath operating part, and coupled to the sheath such that the advance and retract operation of the sheath operating part in a direction of the central axis interlocks with the sheath, and a tilt cam formed at a portion of an outer wall portion of the cam tube and engaging with the operating part, and
the tilt cam moves in the direction of the central axis of the cam tube relative to the operating part, and rotates the sheath operating part around an axis relative to the operating part.

15. The ultrasonic endoscope treatment tool according to claim 6,
wherein when the stylet is seen toward the distal end side from the proximal end side in a delivery direction in which the implant is delivered from the tubular member, the stylet rotates around an axis of the stylet inside the tubular member in a direction opposite to a winding direction of the coiled form of the portion of the implant hooked to the body tissue.

16. The ultrasonic endoscope treatment tool according to claim 6, a winding direction of the implant is opposed to a delivery direction in which the implant is delivered from the tubular member.

17. The ultrasonic endoscope treatment tool according to claim 6, wherein
a first coupling portion is formed at a distal end of the stylet, the first coupling portion being capable of moving in the direction of the longitudinal axis and rotating around the longitudinal axis according to an operation of the operating part,
a second coupling portion is formed at a proximal end of the implant such that the second coupling portion is capable of coupling with the first coupling portion of the stylet,
the implant is capable of advancing and retracting integrally with the stylet by coupling the first coupling portion to the second coupling portion, and
the implant and the stylet are automatically separated from each other, when the implant is advanced integrally with the stylet and the first coupling portion is moved out of the tubular member.

18. The ultrasonic endoscope treatment tool according to claim 17, wherein
the coupling portion of the implant has a though hole and the coupling portion of the stylet has a projection, and the implant is capable of advancing and retracting integrally with the stylet in the state where the projection is inserted into the though hole.

19. The ultrasonic endoscope treatment tool according to claim 1, wherein
a multilayer coil wound around the outer peripheral surface of the tubular member in a circumferential direction and fixed thereto is provided between the tubular member and the sheath.

20. The ultrasonic endoscope treatment tool according to claim 1, wherein
at least a portion of the tubular member is formed from a multilayer coil sheath.

21. The ultrasonic endoscope treatment tool according to claim 1, wherein
at least of a portion of the tubular member is formed from a material having superelasticity.

22. The ultrasonic endoscope treatment tool according to claim 1, wherein
at least a portion of the tubular member is formed from resin.

23. The ultrasonic endoscopic treatment tool according to claim 1,
wherein a fixing member is provided to allows for selection of a state where axial positions of the tubular member and the tubular member slider are fixed and a state where the axial positions are not fixed.

24. The ultrasonic endoscopic treatment tool according to claim 23, further comprising:
a pull-back mechanism that pulls back the tubular member to the inside of the sheath after being moved such that the tubular member protrudes from the sheath,
wherein the pull-back mechanism moves the tubular member relative to the sheath in a direction of the longitudinal axis of the sheath until the distal end of the tubular member is pulled back to the inside of the sheath.

25. The ultrasonic endoscope treatment tool according to claim 1, wherein
the mounting part includes a luer lock connector and a coupling support part,
the luer lock connector is provided to allow the mounting part to be screwed on a port of a forceps channel of the ultrasonic endoscope, and
the coupling support part is provided to couple the ultrasonic endoscope treatment tool to the ultrasonic endoscope, wherein
the coupling support part includes
a frictional engaging portion which is provided in a tubular shape such that the operating part of the ultrasonic endoscope is plugged into the frictional engaging portion and an external surface of the operating part is frictionally engaged with the frictional engaging portion;
a slip-out stopper pin provided to pierce an outer peripheral portion of the port of the forceps channel to prevent the frictional engaging portion from slipping out from the operating part of the ultrasonic endoscope; and
a stopper portion provided to allow a sheath slider of a sheath operating part to be plugged in and to be fixed with a screw.

26. A coupling support part provided to be capable of coupling with an operating part of the ultrasonic endoscope, and coupling a forceps channel of the ultrasonic endoscope with the ultrasonic endoscopic treatment tool according to any one of claims 1-15, 23 to 24, the coupling support part comprising:
a first engaging portion that engages with the external surface of the operating part;
a second engaging portion that engages with the external surface of the ultrasonic endoscope treatment tool; and
a coupling portion that couples together the first engaging portion and the second engaging portion in a positional relationship in which the direction of the central axis of a port of the forceps channel on the side of the operating part of the endoscope coincides with a direction in which the sheath extends from the ultrasonic endoscope treatment tool.

\* \* \* \* \*